(12) United States Patent
Sasada et al.

(10) Patent No.: US 11,990,227 B2
(45) Date of Patent: May 21, 2024

(54) MEDICAL SYSTEM, MEDICAL APPARATUS, AND MEDICAL METHOD

(71) Applicant: Sony Corporation, Tokyo (JP)

(72) Inventors: Shiori Sasada, Kanagawa (JP); Shinji Watanabe, Tokyo (JP); Kenji Yamane, Kanagawa (JP); Yutaka Hasegawa, Kanagawa (JP); Kazuma Takahashi, Chiba (JP)

(73) Assignee: Sony Corporation, Tokyo (JP)

(*) Notice: Subject to any disclaimer, the term of this patent is extended or adjusted under 35 U.S.C. 154(b) by 587 days.

(21) Appl. No.: 17/269,933

(22) PCT Filed: Aug. 28, 2019

(86) PCT No.: PCT/JP2019/033804
§ 371 (c)(1),
(2) Date: Feb. 19, 2021

(87) PCT Pub. No.: WO2020/045536
PCT Pub. Date: Mar. 5, 2020

(65) Prior Publication Data
US 2021/0319881 A1 Oct. 14, 2021

(30) Foreign Application Priority Data

Aug. 31, 2018 (JP) .................................. 2018-162613
Jan. 17, 2019 (JP) .................................. 2019-006222

(51) Int. Cl.
*G16H 30/40* (2018.01)
*G06T 7/00* (2017.01)
*G16H 70/60* (2018.01)

(52) U.S. Cl.
CPC ........... *G16H 30/40* (2018.01); *G06T 7/0012* (2013.01); *G16H 70/60* (2018.01); *G06T 2207/30096* (2013.01)

(58) Field of Classification Search
None
See application file for complete search history.

(56) References Cited

U.S. PATENT DOCUMENTS

2008/0100612 A1   5/2008   Dastmalchi et al.
2010/0265267 A1   10/2010  Schaepe et al.
(Continued)

FOREIGN PATENT DOCUMENTS

EP   2 333 717 A1   6/2011
JP   2011117991 A   6/2011
JP   2014149689 A   8/2014

OTHER PUBLICATIONS

International Search Report and Written Opinion dated Nov. 18, 2019 in connection with International Application No. PCT/JP2019/033804.

*Primary Examiner* — Leon Flores
(74) *Attorney, Agent, or Firm* — Wolf, Greenfield & Sacks, P.C.

(57) ABSTRACT

A medical system comprising: a control part configured to receive pathological image data that is produced by imaging one observation target object and that includes first and second image data, the second image data relating to the observation target object but being different to the first image data, a display control part that causes a displaying part to display thereon the first image data and the second image data; and an annotation processing part that applies an annotation to each of the first image data and the second image data on a basis of inputting by a user.

27 Claims, 19 Drawing Sheets

(56) References Cited

U.S. PATENT DOCUMENTS

| | | |
|---|---|---|
| 2011/0131535 A1 | 6/2011 | Tagami |
| 2014/0201148 A1 | 7/2014 | Doui |
| 2015/0130921 A1 | 5/2015 | Ohashi et al. |
| 2016/0048987 A1 | 2/2016 | Sevenster et al. |
| 2018/0246868 A1 | 8/2018 | Tsujimoto et al. |
| 2019/0164286 A1* | 5/2019 | Hashizume ............ G06T 11/60 |

* cited by examiner

MEDICAL SYSTEM, MEDICAL APPARATUS, AND MEDICAL METHOD

CROSS-REFERENCE TO RELATED APPLICATIONS

This application claims the benefit under 35 U.S.C. § 371 as a U.S. National Stage Entry of International Application No. PCT/JP2019/033804, filed in the Japanese Patent Office as a Receiving Office on Aug. 28, 2019, which claims priority to Japanese Patent Application Number JP2019-006222, filed in the Japanese Patent Office on Jan. 17, 2019 and Japanese Patent Application Number JP2018-162613, filed in the Japanese Patent Office on Aug. 31, 2018, each of which is hereby incorporated by reference in its entirety.

TECHNICAL FIELD

The present disclosure relates to a medical system, a medical apparatus, and a medical method.

BACKGROUND ART

Techniques relating to an annotation applied to a tumor area or the like in medical image data (including pathological image data and the like) have recently been actively developed. For example, NPL 1 below discloses a technique capable of improving the precision of diagnoses by applying accurate annotations to IHC (Immunohistochemistry) image data.

CITATION LIST

Non Patent Literature

NPL 1: Barnes M and other 13 authors, "Wholetumor section quantitative image analysis maximizes between-pathologists' reproducibility for clinical immunohistochemistry-based biomarkers," Laboratory Investigation, Aug. 14, 2017, Volume 97, pp. 1508-1515

SUMMARY

Technical Problem

With the technique of NPL 1, and the like, properly applying an annotation may however be difficult. For example, in the case where a portion to be an annotation applying target is displayed on a display to be small relative to the display, the user switches the whole display to image data whose resolution is higher and thereby applies an annotation. The user however cannot see the portion to be the annotation applying target in a perspective view when the whole display is switched to the image data whose resolution is higher. Moreover, the operation of switching to the image data relating to the observation target object but being different (for example having more detailed visual information relating to the observation target object such as whose resolution is higher) may be troublesome for the user.

The present disclosure was therefore conceived in view of the above circumstances and provides a medical system, a medical apparatus, and a medical method that each are novel and improved and that each can more properly apply an annotation to pathological image data.

Solution to Problem

According to the present disclosure, medical system is provided that includes: a control part configured to receive pathological image data that is produced by imaging one observation target object and that includes first and second image data, the second image data relating to the observation target object but being different to the first image data, a display control part that causes a displaying part to display thereon the first image data and the second image data; and an annotation processing part that applies an annotation to each of the first image data and the second image data on a basis of inputting by a user.

Moreover, according to the present disclosure, a medical apparatus is provided that includes: a control part configured to receive pathological image data that is produced by imaging one observation target object and that includes first and second image data, the second image data relating to the observation target object but being different to the first image data, a display control part that causes a displaying part to display thereon the first image data and the second image data; and an annotation processing part that applies an annotation to each of the first image data and the second image data on a basis of inputting by a user.

Moreover, according to the present disclosure, a medical method executed by a computer is provided. The medical method including the steps of: receiving pathological image data that is produced by imaging one observation target object and that includes first and second image data, the second image data relating to the observation target object but being different to the first image data, causing a displaying part to display thereon the first image data and the second image data; and applying an annotation to each of the first image data and the second image data on a basis of inputting by a user.

According to the present disclosure, a medical system is provided that includes: an imaging apparatus producing pathological image data including first and second image data, the second image data relating to the observation target object but being different to the first image data; and software used in processing for the pathological image data, wherein the software is executed by an information processing apparatus, and thereby realizes causing a displaying part to display thereon the first image data and the second image data, and applying an annotation to each of the first image data and the second image data on a basis of inputting by a user.

According to the present disclosure, the user can perform inputting relating to the annotation, watching both the first image data and the second image data. The present disclosure enables more proper application of the annotation to the pathological image data.

Advantageous Effects of Invention

As described above, according to the present disclosure, an annotation can more properly be applied to the pathological image data.

In addition, the above effect is not necessarily a limiting one, and any one of the effects described in the present specification or any other effects that are understandable from the present specification may be achieve together with the above effect or instead of the above effect.

DESCRIPTION OF EMBODIMENTS

Figure 1:
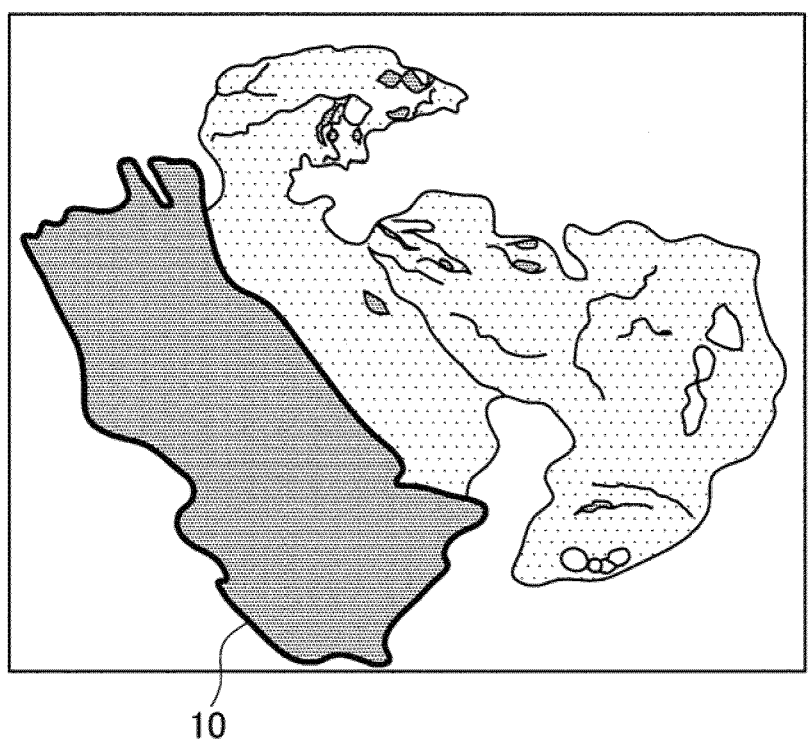
FIG. 1 is a diagram for explaining a specific example of an annotation 10 applied to medical image data.

A preferred embodiment of the present disclosure will be described below in detail with reference to the accompanying drawings. In addition, in the present specification and the drawings, constituent elements having the substantially same function and configuration are given the same reference numeral and will thereby not again be described.

In addition, the description will be made in the following order.

1. Overview
2. Embodiment
  2.1. Configuration
  2.2. Details of Processing Relating to Annotation 10
  2.3. Hardware Configuration
  2.4. Variation of System Configuration
3. Conclusion 1. Overview The overview of the present disclosure will first be described.

To verify effects of a drug in the development of the drug and to give a pathological diagnosis, it is important to accurately calculate the size and the rate of a tumor area, an interstice, or the like, or the dimension of the nucleus in the tissue. Especially, associated with the digitalization of the pathological images and the boom of the cancer immunotherapy using a PD-L1 (Programmed cell Death 1-Ligand 1), and the like, it has become more important to quantify the area of a tumor area, and the distribution and the quantity of dyed cells in the tumor area, using immunostaining or the like using serial sections. Applying an annotation that indicates a tumor area or the like to medical image data is thereby actively performed by doctors. Moreover, as above, a technique of NPL 1 has also been developed according to which the precision of a diagnosis can be improved by applying an accurate annotation to IHC image data. It should be noted that applying an annotation may mean attaching an annotation to an image, embedding an annotation in an image, storing co-ordinates within the image defining an annotation, associating the annotation with a position and/or co-ordinate in the image or the like.

It may however be difficult to properly apply an annotation with the technique of NPL 1 or the like. For example, in the case where a portion to be an annotation applying target is displayed on a display to be small relative to the display, the user applies an annotation by switching the whole display to image data whose resolution is higher, superimposing the image data whose resolution is higher on the original image data, to be displayed, or the like. It should be noted that having image data relating to the observation target object but being different to the first image data is only one example. Other examples include providing more detailed visual information relating to the observation target object, providing different visual characteristics relating to the observation target, applying image data of observation target coloured with a different dye, or using a different imaging technique to that of the original image data. The image data that relates to the observation target object but being different to the first image data may sometimes be hereinafter referred to as an "annotation auxiliary image". The user however cannot see the portion to be the annotation applying target in a perspective view when the whole display is switched to the image data whose, for example, resolution is high. Moreover, the operation of stitching to the image data whose resolution, for example, is high may also be troublesome for the user. Furthermore, even when the annotation auxiliary image is displayed as the superimposition on the display, in the case where the annotation is displayed only in the original image data and is not displayed in the annotation auxiliary image, the user is required to perform the inputting watching the portion displayed in the annotation auxiliary image and the portion to have the annotation actually applied thereto comparing these portions therebetween. It may therefore be difficult to apply an accurate annotation.

The person who discloses this invention finally created the technique according to the present disclosure in view of the above circumstances. A medical system according to the present disclosure, for pathological image data produced by imaging one observation target object and including pieces of image data having plural different resolutions, can cause a displaying part to display thereon first image data having a first resolution of the plural different resolutions and second image data having a second resolution equal to the first resolution, or equal to or higher than the first resolution, and can apply an annotation to each of the first image data and the second image data on the basis of inputting by a user. The user can thereby execute inputting that relates to the annotation, watching both the first image data and the second image data relating to the observation target object but being different to the first image data. The present disclosure therefore enables more proper application of an annotation to the pathological image data.

Moreover, in the medical system according to the present disclosure, control points to be plural points on the annotation are set and the annotation can more properly be produced and corrected by using the control points.

Moreover, a technique of applying an annotation using a machine learning technique has recently been developed while attaching meticulous annotations to a huge amount of medical image data is demanded to produce the learning data for the machine learning, and much time and many workers are therefore necessary.

For this point, in the medical system according to the present disclosure, inputting relating to an annotation and inputting relating to the display of the first image data or the second image data are realized each using a method different from that of each other. More specifically, in the medical system according to the present disclosure, the inputting relating to the annotation is performed by one hand of the user and the inputting relating to the display of the first image data or the second image data is performed by the other hand thereof. This input method resembles the input method conventionally performed by doctors when the doctors apply annotations and the medical system according to the present disclosure can therefore more intuitively and more efficiently realize the work by the user such as a doctor. Moreover, the medical system according to the present disclosure has a configuration for the user to more easily perform the inputting especially for annotations drawn freehand.

On the basis of the above, the medical system according to the present disclosure enables more proper application of an annotation to the pathological image data and furthermore enables improvement of the quality and the efficiency of drug development and a pathological diagnosis.

2. Embodiment

The overview of the present disclosure has been described in the above. An embodiment of the present disclosure will next be described.

A medical system 100 according to the present embodiment is an information processing system that is used when a user applies an annotation 10 to medical image data, and includes, for example, a medical microscope (such as, for example, an optical microscope), an apparatus connected for communication to the medical microscope and the like. In addition, the case where the medical image data to which the annotation 10 is applied by the medical system 100 is pathological image data will hereinafter be described as an example while the medical image data to which the annotation 10 is applied only has to be certain image data relating to medical care and is not necessarily limited to the pathological image data. For example, the medical image data to which the annotation 10 is applied may be radiographic image data or ultrasonic image data. In other words, the medical image data to which the annotation may be applied is captured using different imaging techniques.

Concerning the above, a specific example of the annotation 10 applied by the medical system 100 to the medical image data will be described with reference to FIG. 1. As depicted in FIG. 1, the annotation 10 according to the present embodiment is applied to indicate an observation target object included in the pathological image data and is applied to surround a tumor area that is the observation target object. In other words, the annotation 10 according to the present embodiment is applied to indicate a closed region included in the pathological image data (such as, for example, a region having the tumor area that is the observation target object, and the like imaged therein). The annotation 10 is used for the output of the area of the region to which the annotation 10 is applied, the probability for the observation target object to be a tumor, the positivity of the tumor, various scores, and the like, is used in the pharmaceutical field for counting the number of immune cells in the tumor area and the number of cells in the tumor margin, and the like, and the selection of patients for a medicine on the basis of the number of immune cells infiltrating into the tumor, and the like are thereby performed. Moreover, it is known that the precision of a cancer genetic test is improved by determining and cutting out a tumor area (desirably, a tumor area including a specific number or more of idioblasts) and the like from a pathological section in the cancer generic test and, in this case, the annotation 10 is usable for the cutting out of the tumor area from the pathological section, the counting of the number of cells inside the tumor, and the like.

2.1. Configuration

Figure 2:
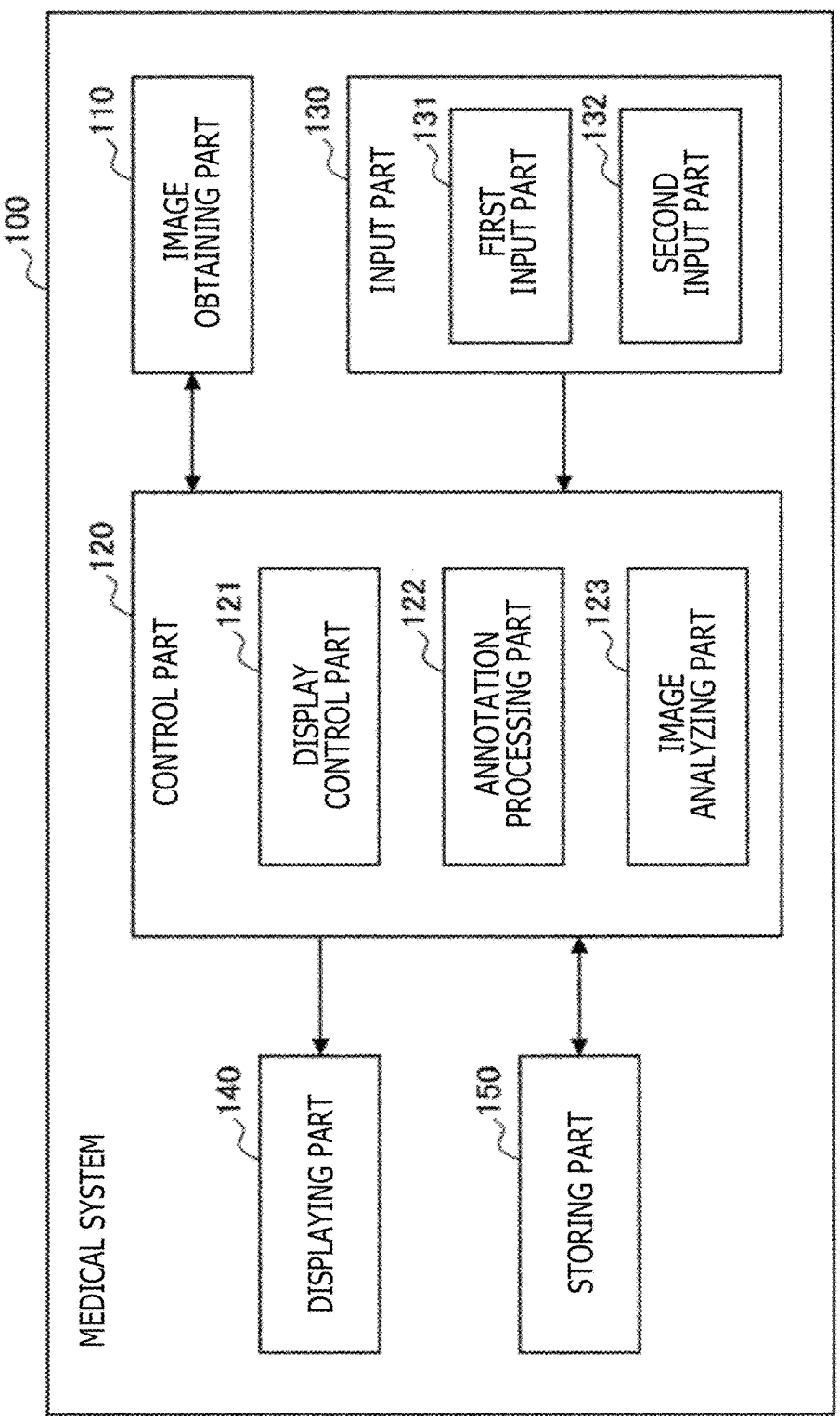
FIG. 2 is a block diagram depicting an example of the configuration of a medical system 100.

An example of the configuration of the medical system 100 will be described with reference to FIG. 2. FIG. 2 is a block diagram depicting an example of the configuration of the medical system 100 according to the present embodiment. As depicted in FIG. 2, the medical system 100 includes an image obtaining part 110, a control part 120, an input part 130, a displaying part 140, and a storing part 150.

Image Obtaining Part 110

The image obtaining part 110 is configured to obtain pathological image data. The image obtaining part 110 may obtain the pathological image data by including an image sensor (such as, for example, a CMOS (Complementary Metal Oxide Semiconductor) or a CCD (Charge Coupled Device)) and functioning as a medical microscope, or may obtain the pathological image data by communication with an external medical microscope.

Figure 3:
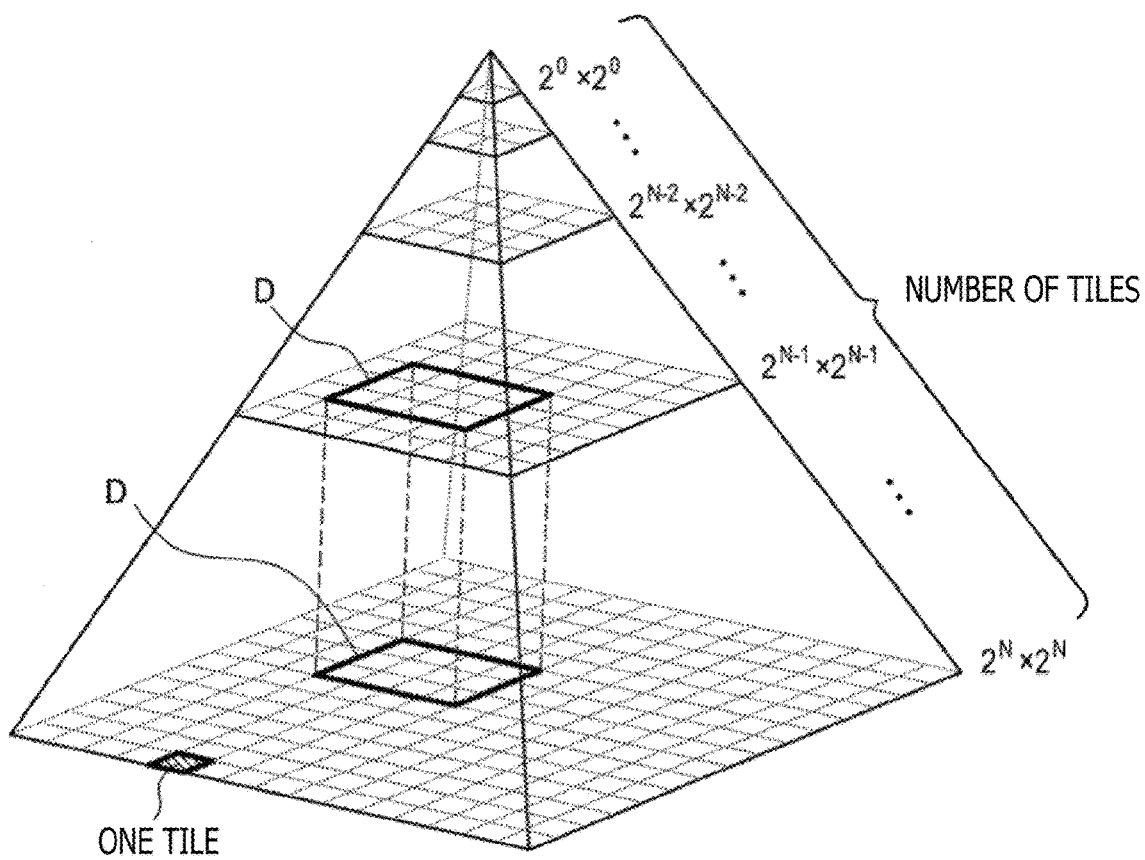
FIG. 3 is a diagram depicting a pyramid structure for explaining pathological image data and the principle of displaying this data.

Concerning the above, the details of the pathological image data obtained by the image obtaining part 110 will be described with reference to FIG. 3. FIG. 3 is a diagram depicting a pyramid structure for explaining the pathological image data and the principle of displaying this data. The pathological image data having the pyramid structure in FIG. 3 is data that is produced by imaging one observation target object and that includes pieces of image data having plural different resolutions. In the case of FIG. 3, this explains the example embodiment where the relation to the observation target object but being different to the first image data is visual information having a higher image resolution. Furthermore, the pieces of image data included in the pathological image data are represented by the pyramid structure in FIG. 3 in accordance with the resolutions. At the lowermost position of the pyramid structure, the image data having the highest resolution (having the largest data size) is arranged and, at the uppermost position of the pyramid structure, the image data having the lowest resolution (having the smallest data size) is arranged. The highest resolution is, for example, 50×50 (Kpixel: kilo-pixel) or 40×60 (Kpixel), and the lowest resolution is, for example, 256×256 (pixel) or 256×512 (pixel). In addition, the resolutions of the pieces of the image data are not limited to these.

When the displaying part 140 described in a section below displays thereon these pieces of image data each at, for example, 100% (displays thereon each with the number of physical dots equal to the number of pixels of the image data), the image data having the highest resolution (having the largest data size) is displayed in the largest size and the image data having the lowest resolution (having the smallest data size) is displayed in the smallest size. Concerning this, in FIG. 3, the display range of the displaying part 140 is indicated by "D." Moreover, the pieces of image data included in the pathological image data are managed using "tile" as the unit, that is the unit of a predetermined size. The size of one tile may be, for example, 256×256 (pixel) while the size is not limited to this.

The pathological image data obtained by the image obtaining part 110 is stored by the storing part 150 therein described in a section below. In addition, it should be noted that the pyramid structure described above is a concept that is used to absolutely describe the pathological image data. Practically, in the pathological image data, the pieces of image data having the plural different resolutions and pieces of information relating to these resolutions only have to be respectively correlated with each other.

Control Part 120

The control part 120 is configured to generally control the overall processes executed by the medical system 100. For example, the control part 120 produces a control signal, provides the control signal to each of the configurations, and can thereby control starting up and stoppage of each of the configurations. In addition, the function of the control part 120 is not especially limited. For example, the control part 120 may control the processes generally executed by each of various types of server, a general-purpose computer, a PC (Personal Computer), a tablet PC, and the like (such as, for example, the processes relating to an OS (Operating System)).

As depicted in FIG. 2, the control part 120 includes a display control part 121, an annotation processing part 122, and an image analyzing part 123.

Display Control Part 121

The display control part 121 is configured to cause the displaying part 140 to display thereon first image data and second image data. It is noted that in the disclosure, the second image data relates to the observation target object but is different to the first image data. The second image data is the data used as the annotation auxiliary image described above (in the present embodiment, described as "annotation auxiliary image 20").

Figure 4:
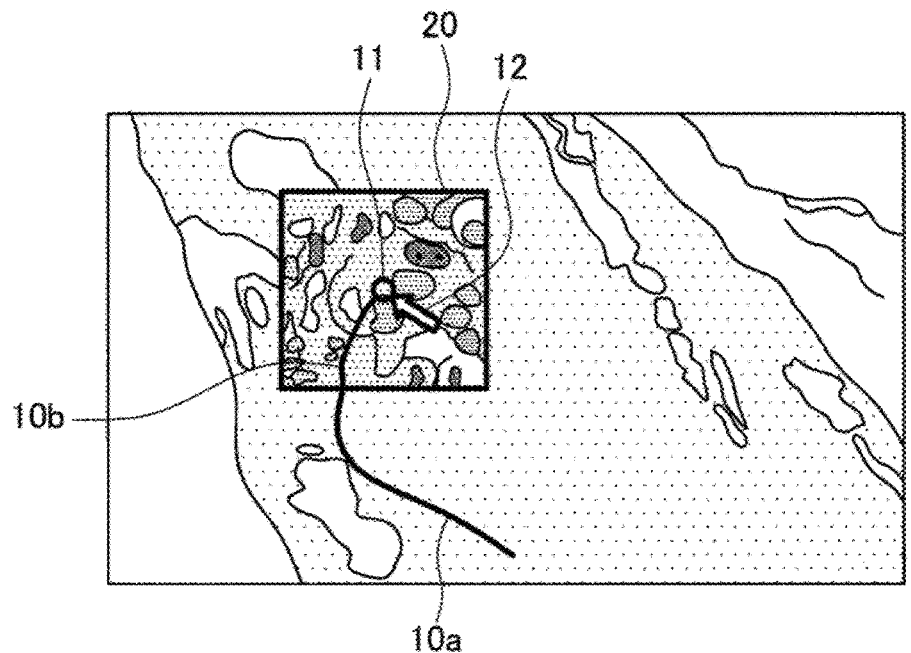
FIG. 4 is a diagram for explaining the details of display control executed by a display control part 121.
Figure 5:
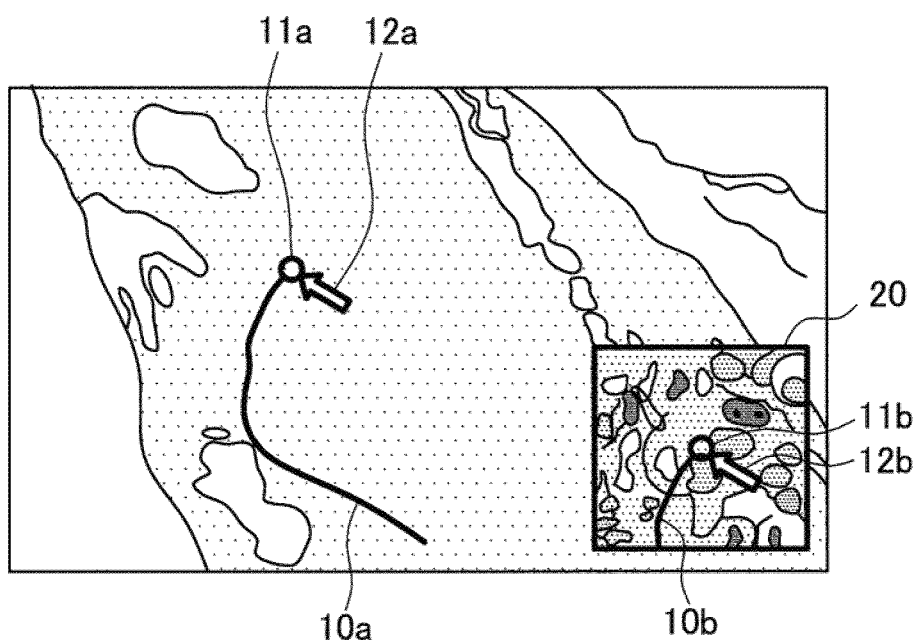
FIG. 5 is a diagram for explaining the details of the display control executed by the display control part 121.

Concerning the above, the details of the display control executed by the display control part 121 will be described with reference to FIG. 4 and FIG. 5. As depicted in FIG. 4 and FIG. 5, the display control part 121 superimposes the second image data (the annotation auxiliary image 20) on the first image data and causes these pieces of data to be displayed. The user can perform meticulous inputting relating to the annotation 10 using the second image data, watching the observation target object in a perspective view using the first image data, by the fact that the second image data relates to the observation target object but being different to the first image data are displayed as above. Moreover, compared to the case where image data produced simply by electronically zooming the first image data is provided as one example of providing the second image, the display control part 121 can provide higher-definition image data to the user. Moreover, as depicted in FIG. 5, the second image data is displayed at a position distant from the input position (the cursor position) and thereby the first image data in the vicinity of the input position does not need to be hidden by the second image data. In addition, the display position of the second image data is not especially limited and, for example, the second image data may be displayed in the vicinity of the center of the first image data, or may be displayed in a display area or on a display that is different from that of the first image data without being superimposed on the first image data.

Moreover, as depicted in FIG. 4, the display control part 121 can cause a position in the first image data for which the inputting is performed by the user (an input point 11 in FIG. 4 and an input point 11a in FIG. 5) and a position in the second image data for which the inputting is performed by the user (the input point 11 in FIG. 4 and an input point 11b in FIG. 5) to be superimposed on each other and to be displayed (in other words, cause these positions to be displayed at a substantially same position). The second image data is thereby displayed at the position that the user sees to apply the annotation 10 to and the user can therefore more easily perform the inputting without changing the visual line thereof. In addition, the position in the first image data for which the inputting is performed by the user (the input point 11 in FIG. 4 and the input point 11a in FIG. 5) and the position in the second image data for which the inputting is performed by the user (the input point 11 in FIG. 4 and the input point 11b in FIG. 5) may not necessarily be displayed at the substantially same position. For example, the second image data may be displayed in the vicinity of the position in the first image data for which the inputting is performed by the user to the extent that the position in the first image data is not hidden thereby.

Moreover, the color (such as, for example, the transparency degree and the like), the size, or the shape of the display of the second image data superimposed on the first image data are not especially limited while the first image data displays the region of the observation target object that is larger than that of the second image data, and the user can apply the annotation watching the observation target object in a perspective view using the first image data by the fact that the observation target object is displayed in a display region that is larger than that of the second image data. In the case where the first image data and the second image data have the equal resolution and are displayed at display positions that are matched with each other, the display control part 121 may cause the second image data that is superimposed on the first image data, to be displayed to be see-through thereon. Moreover, the size of the second image data may freely be set in the display field angle (or in the first image data). Furthermore, the shape of the second image data may be a rectangular shape, a circular shape, a shape designated free-hand by user inputting, or the like. In the case where the shape of the second image data is a rectangular shape, it is desirable that the aspect ratio of the second image data is substantially equal to the aspect ratio of the displaying device (the aspect ratio of the first image data in the case where the first image data is displayed on the overall screen of the displaying device). In the case where the second image data has, for example, a substantially square shape, the user may feel that the information amount obtained from the second image data is small while this problem can be avoided by setting the aspect ratio of the second image data to be substantially equal to the aspect ratio of the displaying device. The color (such as, for example, the transparency and the like), the size, or the shape of the display of the second image data may be switched on the basis of the selection by the user.

In addition, the input position in the first image data is hidden by the second image data in the scheme in FIG. 4 while the user can immediately check the annotation 10 also on the first image data (or the user can check the annotation 10 applied to the region not having the second image data superimposed thereon) simultaneously when the inputting relating to the annotation 10 comes to an end, by the fact that the annotation 10 is also applied in real time to the first image data. It is therefore desirable that the annotation 10 is also applied in real time to the first image data, while the attachment is not limited to this and the annotation 10 may be applied to the first image data simultaneously when the inputting relating to the annotation 10 comes to an end.

Moreover, the display control part 121 can cause the displaying part 140 to display thereon the second image data on the basis of the inputting by the user (such as, for example, inputting to apply the annotation 10 by the user). For example, during pressing down of a button or the like by the user (or during clicking a mouse and dragging it by the user), the display control part 121 may cause the displaying part 140 to display thereon the second image data. Moreover, the display control part 121 may switch between a "display mode" in which the second image data is always kept displayed and a "non-display mode" in which the second image data is not displayed on the basis of an instruction by the user. The second image data is not displayed by these processes when any inputting to apply the annotation 10 is not performed and the user can therefore easily watch the observation target object in a perspective view using the first image data.

In addition, the position in each of the pieces of image data for which the user performs the inputting is displayed in accordance with the position in the image data relating to the observation target object but being different to the first image data, such as having the more detailed visual information, for example, higher resolution of the displayed pieces of image data. More specifically, the position in the first image data for which the inputting is performed by the user (the input point 11 in FIG. 4 and the input point 11a in FIG. 5) is displayed in accordance with the position in the second image data for which the inputting is performed by the user (the input point 11 in FIG. 4 and the input point 11b in FIG. 5). The user can thereby perform the inputting with the more detailed visual information, such as highest resolution of the resolutions that the displayed pieces of image data have (in other words, the user can apply the annotation 10 with the more detailed visual information, such as highest resolution). In addition, even in the case where the image data having the more detailed visual information, such as highest resolution is not displayed, the positions in the pieces of image data for which the inputting is performed by the user may be displayed in accordance with the position in the image data having the more detailed visual information, such as highest resolution.

In the event that the relation to the observation target object but being different to the first image data is more detailed visual information such as a higher resolution image, the first image data and the second image data may each have a resolution different from that of each other for one observation target object. The ratios of the first resolution that the first image data has and the second resolution that the second image data has are not especially limited while, in the case where the second resolution higher than the first resolution is set, when the second resolution is excessively higher than the first resolution, the positional relation becomes difficult to understand between the first image data and the second image data. The second resolution is therefore desirably approximately a two-fold to approximately an eight-fold value of the first resolution, and is more desirably approximately a two-fold to approximately a four-fold value thereof.

Moreover, the second resolution that the second image data has may be equal to the first resolution. This is because, in the case where, for example, the first image data has an extremely high resolution (such as, for example, a 4K resolution), the second image data having the extremely high resolution equal to that of the first image data is applied with predetermined image processing and is displayed and, the effect like the above is thereby achieved. The "predetermine image processing" may include, for example, the electronic zooming, contrast adjustment, and the like. Moreover, in the case where the first resolution is significantly low, or the like, the second image data may be image data produced by applying a super-resolution process to the first image data.

Moreover, the first image data and the second image data may be pieces of image data that focus positions different from each other on the one observation target object. In other words, the first image data and the second image data may be pieces of image data having visual characteristics different from each other.

For example, in the case where the first image data includes a portion that is not focused such as the case where a section to be the observation target object is bent or the case where the section is uplifted, the image data having the portion set to be focused may be displayed as the second image data (in other words, the second image data may be displayed whose focal position in the depth direction is different from that of the first image data).

Moreover, the first image data and the second image data may each be image data having therein an object different from that of each other, dyed by a dyeing reagent. In other words, the first image data and the second image data may be pieces of image data having visual characteristics different from each other. This second image data relates to the observation target object but is different to the first image data. For example, in the case where the effects of a drug is determined in drug development, or the like, the molecular characteristics of the cells are often observed first using an IHC stained image. The local existence, the distribution, and the like of the desired cells are observed in a perspective view using the IHC image and, for a specific region, the morphological characteristics are thereafter observed using the HE stained image. In this case: an immuno-stained image data indicating the immune state of the tissue such as the IHC stained image data, or specially stained image data visualizing specific tissue elements for each of the purposes may be displayed as the first image data; and general stained image data indicating the form of the tissue such as HE (Hematoxylin-Eosin) stained image data may be displayed as the second image data. For example, in the case where an observation target object is dyed by a dyeing reagent capable of dyeing also any object in addition to the tumor cells (such as, for example, Ki67), the user cannot accurately recognize the form of the tumor cells in the observation target object using only the IHC stained image data. The user can accurately recognize the form of the tumor cells using the HE stained image data by the fact that the HE stained image data is displayed as the second image data.

Figure 6:
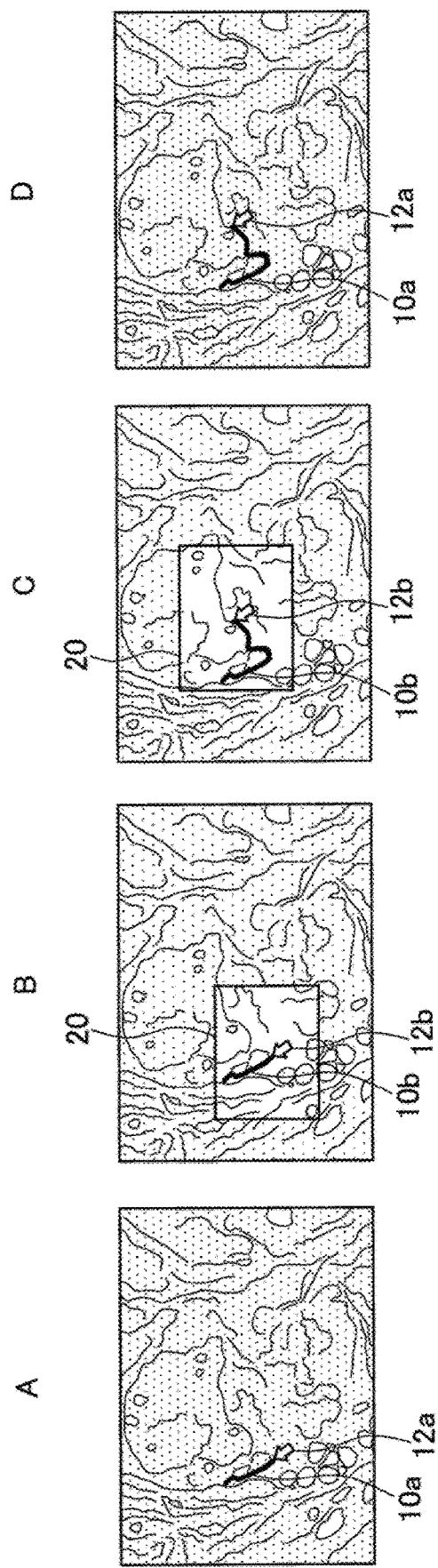
FIG. 6 depicts diagrams for explaining the details of the display control executed by the display control part 121.

For example, in the case where an affected area is identified such as a diagnosis, the morphological characteristics are often observed first using the HE stained image. The positional relation between the affected area and the organs is identified using the HE stained image and the molecular characteristics are thereafter observed for a specific region using the IHC stained image and the specially stained image. Different from the above, in this case, the general stained image data (such as, for example, the HE stained image data) may be displayed as the first image data and the immuno-stained image data (such as, for example, the IHC stained image data) or the special stained image data (such as, for example, PAS stained image data) may be displayed as the second image data. Concerning this, a specific example of the case where the IHC stained image data to be the second image data is superimposed on the HE stained image data to be the first image data will be described with reference to FIG. 6. In A of FIG. 6, it is assumed first that only the HE stained image data to be the first image data is displayed and the user applies an annotation 10*a* by moving a cursor 12*a* using only the HE stained image data. Concerning this, in the case where the user considers, for example, that the user desires to apply the annotation 10*a* to a point whose stain state of HER2 is strong, the user cannot accurately recognize the point using only the HE stained image data. As depicted in B of FIG. 6, the display control part 121 causes the IHC stained image data that is the second image data (the annotation auxiliary image 20) to be superimposed thereon and displayed. As depicted in C of FIG. 6, the user can thereby accurately recognize the point whose stain state of HER2 is strong using the IHC stained image data and can thereby apply an annotation 10*b* and, when the IHC stained image data is caused not to be displayed, as depicted in D of FIG. 6, the annotation 10*a* is also applied to the HE stained image data. In addition, in the example of FIG. 6, because a cursor 12*b* in the IHC stained image data is set to be able to continuously be arranged at the center of the IHC stained image data, the display position of the IHC stained image data therefore moves in the HE stained image data as the annotation 10*b* is gradually drawn from B to C of FIG. 6 (in addition, the display form of the IHC stained image data is not limited to this).

Moreover, in the case where observation is desired for different molecular characteristics of a cell, different types of IHC stained image data may be displayed as the first image data and the second image data. For example, the IHC stained image data having CD4 dyed therein may be superimposed on the IHC stained image data having CD8 dyed therein. The user can thereby accurately recognize any presence or absence, and the position of both of the positive cells of CD8 and CD4. For example, it is known that the probability of survival is high when the labeling index of the growth factor Ki-67 of the CD8-positive T-cell in a tumor is high, and the user can mark the cells, can apply the annotation 10, and the like confirming whether or not both CD8 and CD4 are labelled. Furthermore, the user can also perform a quantification analysis for the positional relation between, the area of each of, and the like of CD8 and CD4 as post-processes. In addition, the target of the dyeing is not limited to the combination of CD8 and CD4. For example, the target of the dyeing may be a combination of CD8 and CK (Cytokeratin), CD8 and CD3, HER2 and ER•PgR, or the like (and surely is not limited to the above combinations). These combinations facilitate the determination relating to the probability of survival and the treatment method. Moreover, for each of these combinations, the target, the reagent, the method of the dyeing are not limited to the above and may be those only when the desired object to be imaged can be identified using those. The section for the imaging may be the same one or different sections may be used (such as, for example, serial sections).

Moreover, at least either one of the first image data or the second image data may be the image data to display therein the analysis result (such as, for example, the result of the marking made on a positive nucleus, a heat map, and the like). For example, the user may correct the annotation 10 applied to the membrane on the basis of the analysis result for the nucleus, may correct the annotation 10 applied to the membrane on the basis of the analysis result for the nucleus, and the like by the fact that either one of the first image data or the second image data is the IHC stained image data enabling recognition of the nucleus of one observation target object and the other is the IHC stained image data enabling recognition of the membrane of the same one observation target object. In addition, the "analysis result" may be the result of an analysis automatically executed on the basis of the machine learning technique, the AI technique, and the like, or may be the result of an analysis conducted by the user.

Figure 7:
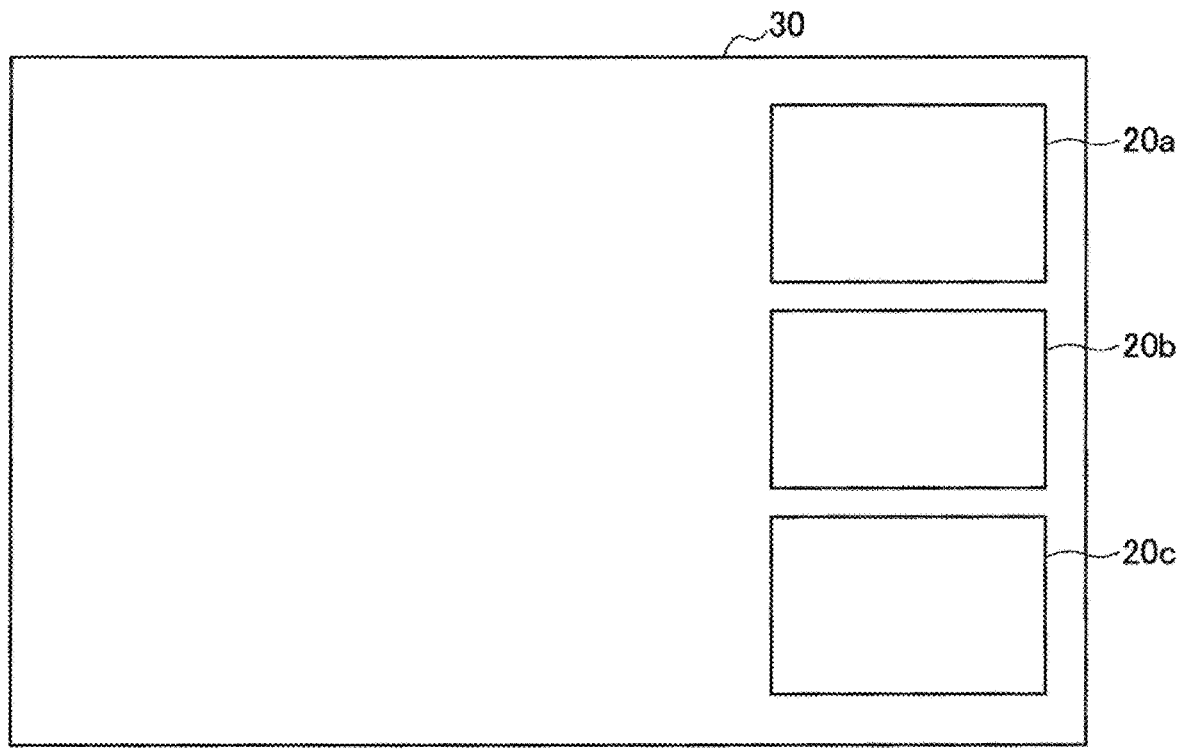
FIG. 7 is a diagram for explaining the details of the display control executed by the display control part 121.

Concerning the above, the second image data may be two or more pieces of image data whose display contents are different from each other. More specifically, the display control part 121 may switch to the second image data displayed in one annotation auxiliary image 20 on the basis of a predetermined input (such as, for example, pressing down of a button by the user) after superimposing the one annotation auxiliary image 20 on the first image data. Moreover, as depicted in FIG. 7, the display control part 121 may superimpose plural annotation auxiliary images 20 displaying therein the pieces of second image data whose display contents are different from each other (that are an annotation auxiliary image 20*a* to an annotation auxiliary image 20*c* displayed in first image data 30 in the example of FIG. 7) on the first image data. Moreover, the display control part 121 may cause the plural annotation auxiliary images 20 displaying pieces of second image data whose display contents are different from each other, to be displayed outside the first image data after superimposing one annotation auxiliary image 20 on the first image data. In this case, when the user selects any one of the pieces of second image data displayed outside the first image data, the second image data displayed in the annotation auxiliary image 20 superimposed on the first image data may be switched to the selected image data. As above, for example, in the case where the IHC stained image data is displayed as the first image data, the user can cause the HE stained image data, the image data displaying the analysis result, and the like to be displayed as the second image data, by using the two or more pieces of image data whose display contents are different from each other as the second image data to be superimposed. Moreover, the user can also cause plural pieces of second image data having plural resolutions different from the resolution of the first image data, to be displayed. To perform comparing various pieces of data is required to the work of applying the annotation 10 to the pathological image data and it can therefore be stated that it is especially useful that the two or more pieces of image data whose display contents are different from each other are used as the second image data. In addition, the plural annotation auxiliary images 20 are placed side by side in the longitudinal direction on the right side in the first image data in the example of FIG. 7 while the positions for the plural annotation auxiliary images 20 to be displayed and the direction therefor to be placed side by side are not especially limited.

The second image data is image data obtained under the imaging conditions (the setting of the imaging apparatus) different from those of the first image data for the same one observation target, image data produced by applying image processing to the first image, or image data produced by imaging a tissue obtained from the same one tissue block as that of the observation target of the first image data. As described above, the accurate application of the annotation can be enabled by using image data having high recognizability for the observation target as the second image data, such as: high quality, high definition, or high image quality image data such as image data having a higher resolution than that of the first image data or image data having a specific imaging object more sharply focused therein; or high-contrast image data, electronically zoomed image data, or image data including differently stained portions. In other words, the second image data relates to the observation target object but is different to the first image data.

Annotation Processing Part 122

The annotation processing part 122 is configured to apply the annotation 10 to each of the first image data and the second image data on the basis of the inputting by the user. More specifically, in the case where the user performs free-hand inputting using the input part 130, the annotation processing part 122 applies the annotation 10 that is free-hand-drawn on the basis of the inputting, to each of the first image data and the second image data. The user can thereby perform the inputting relating to the annotation 10 watching both the first image data and the second image data.

In addition, the approach used by the annotation processing part 122 to apply the annotation 10 to each of the first image data and the second image data is not especially limited. As an example, the annotation processing part 122 may apply the annotation 10 to either one of the first image data or the second image data on the basis of the inputting by the user and to the other thereof using SAL (Stain Alignment). For example, in the case where the annotation processing part 122 applies the annotation 10 to the second image data on the basis of the inputting by the user, the annotation processing part 122 may also apply the annotation 10 to the first image data by executing the process of SAL on the basis of the position information of the point at which the annotation 10 is applied. Concerning this, in the case where the first image data and the second image data are pieces of image data produced by imaging serial sections, pieces of image data produced by imaging the same one section and differing the focal positions from each other in the depth direction, or the like (in other words, in the case where objects having different forms are imaged in the pieces of image data), partial alignment is repeated for plural times for the pieces of image data in the process of SAL. In addition, in the case where the first image data and the second image data are pieces of image data that are produced by imaging the same one section and that have the equal focal distance in the depth direction (in other words, in the case where the objects having the same form are imaged in the pieces of image data), the annotation 10 is applied to the same positions in the first image data and the second image data by matching the position coordinates of these pieces of image data with each other.

Moreover, the annotation processing part 122 determines the timing at which the user causes a pen to touch a tablet in the case where the input part 130 described in a section below includes the pen-table, or the timing at which the user starts dragging using a mouse in the case where the input part 130 includes the mouse, to be the starting timing of the inputting relating to the annotation 10, and starts the production of the annotation 10. The annotation processing part 122 determines the timing at which the user moves the pen away from the tablet or the timing at which the user finishes the dragging, to be the ending timing of the inputting relating to the annotation 10, and ends the production of the annotation 10. Within a predetermined time period from the timing at which the user moves the pen away from the tablet or the timing at which the user finishes the dragging, the annotation processing part 122 may determine that the inputting relating to the annotation 10 still continues. In this case, the annotation processing part 122 may produce the annotation 10 to connect the position at which the pen is caused by the user to move away from the tablet and the position at which the pen is caused by the user to again touch the tablet to each other, or to connect the position at which the dragging is caused by the user to come to an end and the position at which the dragging is caused by the user to again start to each other.

Moreover, as depicted in FIG. 4 and FIG. 5, the annotation processing part 122 may apply not only the annotation 10 but also may concurrently attach the cursor 12 (the cursor 12a and the cursor 12b in FIG. 5) that indicates the input point 11 (the input point 11a and the input point 11b in FIG. 5) at which the inputting is performed by the user. The user can thereby easily recognize the input point 11 and can therefore smoothly perform the inputting relating to the annotation 10. In addition, the cursor 12 is desirably an icon such as a small arrow or a small pencil indicating the position or co-ordinate at which the inputting is performed by the user (such as, for example, an icon of 60 px or smaller and desirably 32 px or smaller) or an icon such as a circular icon which is a small occlusion (an image is hidden) while the cursor 12 is not limited to this. The annotation is then associated with the position/co-ordinate so that the annotation can be later easily viewed by the user.

Concerning to the above, the annotation processing part 122 sets the control points 13 that are plural points on the annotation 10 (that may each be referred to as "CP 13") and executes the production and the correction of the annotation 10 using the control points 13. The details of the processing executed by the annotation processing part 122 will separately be described in a section below.

Image Analyzing Part 123

The image analyzing part 123 is configured to analyze image data included in the pathological image data. More specifically, the image analyzing part 123 realizes various types of functions by analyzing the first image data or the second image data (or pieces of image data other than the first image data and the second image data, that are included in the pathological image data).

The contents of the functions realized by the image analyzing part 123 is not especially limited. For example, the image analyzing part 123 can realize identification of the area in the annotation 10 and the observation target object that is present inside or outside the annotation 10, counting of the number of observation target object present inside or outside the annotation 10, evaluation of the gap between the annotation 10 and the observation target object, the segmentation (region dividing based on the observation target object), or the like, by analyzing the image data. In addition, the image analyzing part 123 and the annotation processing part 122 can execute the processing in proper cooperation with each other. For example, after the image analyzing part 123 evaluates the gap between the annotation 10 and the observation target object, the annotation processing part 122 may execute correction of the annotation 10 and the like when necessary (in the case such as where the gap is larger than a predetermined value, or the like).

Input Part 130

The input part 130 is configured to receive the inputting by the user. As depicted in FIG. 2, the input part 130 includes a first input part 131 and a second input part 132. In addition, the input part 130 may include various types of input mechanism in addition to the first input part 131 and the second input part 132 described below. For example, the input part 130 may include a sound input mechanism and the like.

First Input Part 131

Figure 8:
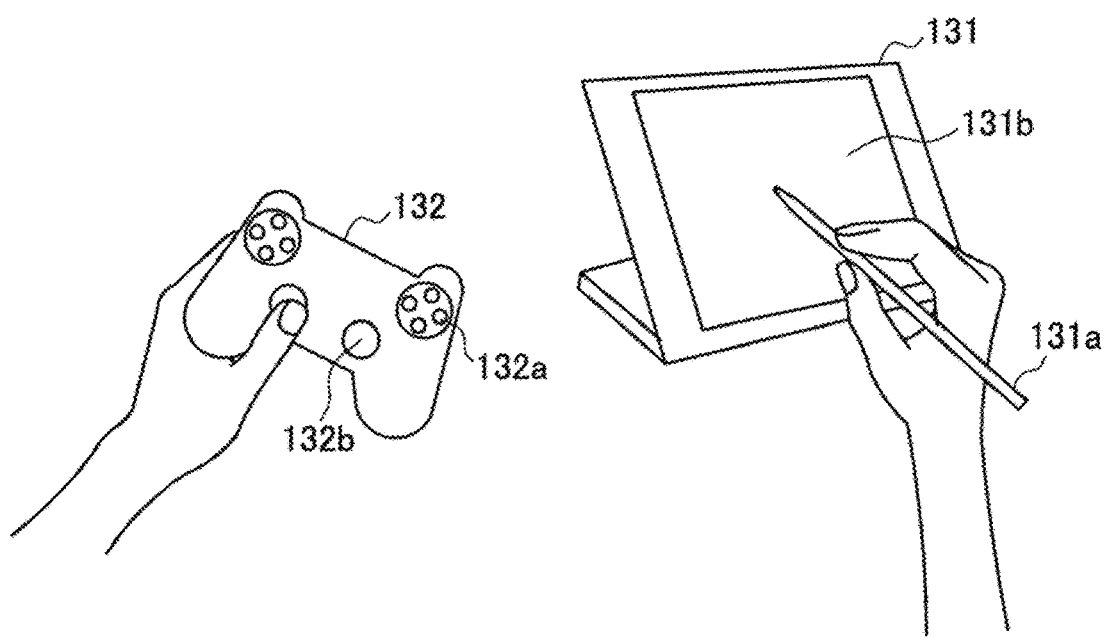
FIG. 8 is a diagram for explaining a specific example of the apparatus configuration.

The first input part 131 is configured to receive the inputting relating to the annotation 10 by the user. Concerning this, a specific example of the first input part 131 will be described with reference to FIG. 8. As depicted in FIG. 8, into the first input part 131, inputting can be performed by touching of a pen 131a or the like, and the first input part 131 may be an apparatus including a touch panel 131b capable of displaying the first image data and the like (such as, for example, a pen-tablet or the like). The inputting by the pen 131a or the like (the inputting by free-hand especially) enables much intuitive inputting compared to the inputting by a mouse or the like, and can reduce the physical load. In addition, the type and the shape of the first input part 131 are not limited to those depicted in FIG. 8. For example, the first input part 131 may include a keyboard, a lever, and the like.

Second Input Part 132

The second input part 132 is configured to receive the inputting relating to the displaying of the first image data or the second image data, by the user. Concerning this, a specific example of the second input part 132 will be described with reference to FIG. 8. As depicted in FIG. 8, the second input part 132 may be an apparatus including buttons 132a, sticks 132b, and the like (such as, for example, a controller). In addition, similar to the first input part 131, the type and the shape of the second input part 132 are not limited to those depicted in FIG. 8.

The user may select, switch, or the like the mode of the medical system 100 by operating the buttons 132a and the sticks 132b. For example, the user may switch between a "display mode" in which the second image data is always kept displayed and a "non-display mode" in which the second image data is not displayed by pressing down the button 132a or inclining the stick 132b in a predetermined direction (in addition, it is assumed that these modes can be switched therebetween regardless of whether or not the annotation 10 is currently produced, and the switching is surely not limited to this). The user can thereby more easily perform the inputting relating to the annotation 10. More specifically, the user can cause the second image data to be displayed at a necessary timing without performing any operation to switch the overall display to image data having a higher resolution or having a more detailed visual information relating to the observation target object for example.

Figure 9:
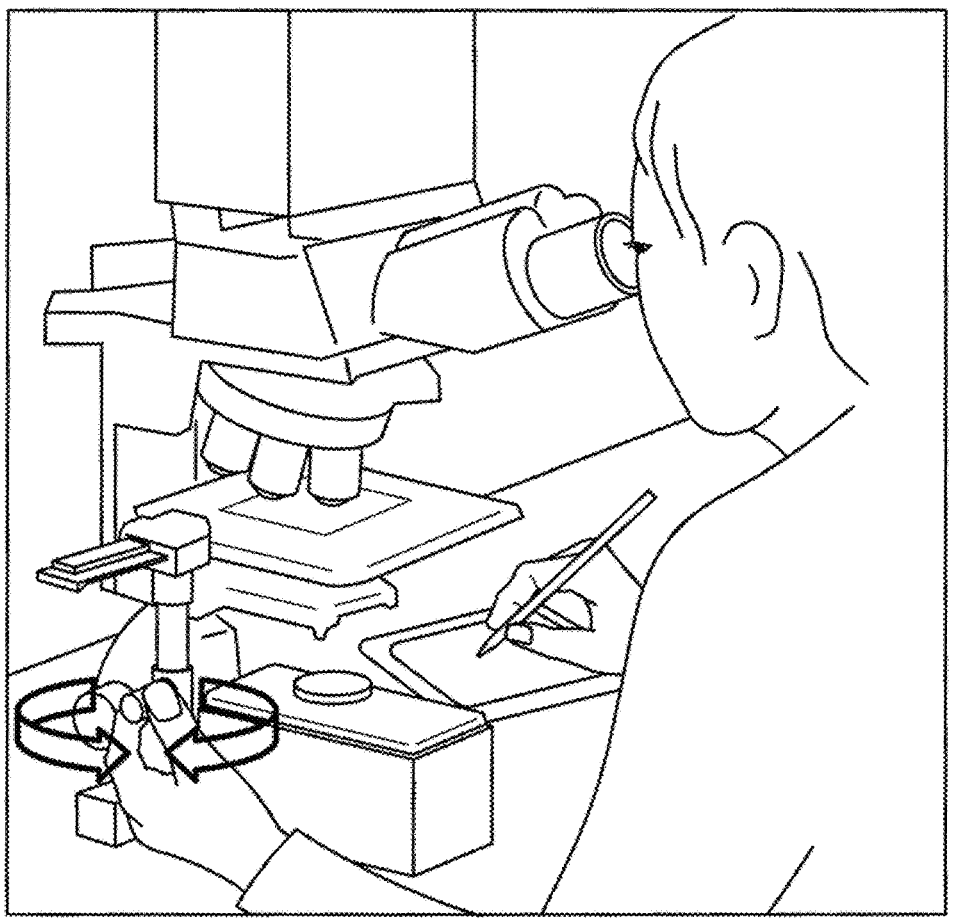
FIG. 9 is a diagram for explaining an input method conventionally executed by doctors when the doctors each apply an annotation 10.
Figure 10:
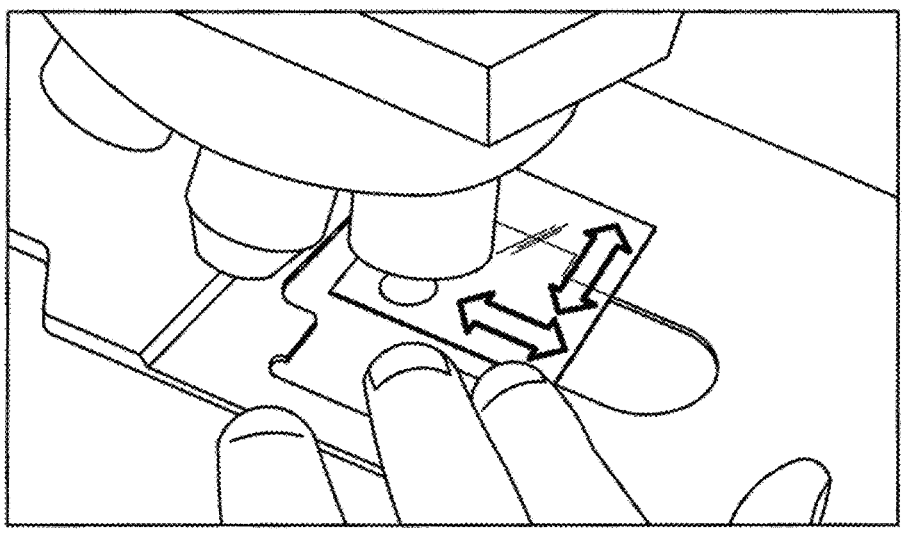
FIG. 10 is a diagram for explaining the input method conventionally executed by the doctors when the doctors each apply the annotation 10.

Either one of the first input part 131 and the second input part 132 described above receives the inputting by the right hand of the user and the other one receives the inputting by the left hand of the user. This input method is similar to the input method conventionally executed by doctors when the doctors apply annotations 10, and the user such as a doctor can more intuitively and more efficiently perform the inputting. FIG. 9 and FIG. 10 depict an aspect of the inputting conventionally performed by doctors when the doctors each apply the annotation 10. For example, as depicted in FIG. 9, doctors each conventionally perform free-hand inputting and the like using a dedicated pen (or a mouse), or the like as the inputting relating to the annotation 10 using one hand (the right hand in FIG. 9) and rotates a nob (a dial) as the inputting relating to the display of the image data (such as, for example, change of the display range (change in the upward, downward, rightward, or leftward direction), a change of the resolution (enlarging or shrinking), or focusing) using the other hand (the left hand in FIG. 9). Moreover, for the inputting relating to the display of the image data, for example, as depicted in FIG. 10, doctors each conventionally move a slide glass (a change of the display range) or the like using one hand (the left hand in FIG. 10). In the present embodiment, as is conventionally performed by doctors, the inputting relating to the annotation 10 and the inputting relating to the display of the first image data or the second image data are each performed by an individual hand and the user such as a doctor can thereby more intuitively and more efficiently perform the inputting.

Figure 11:
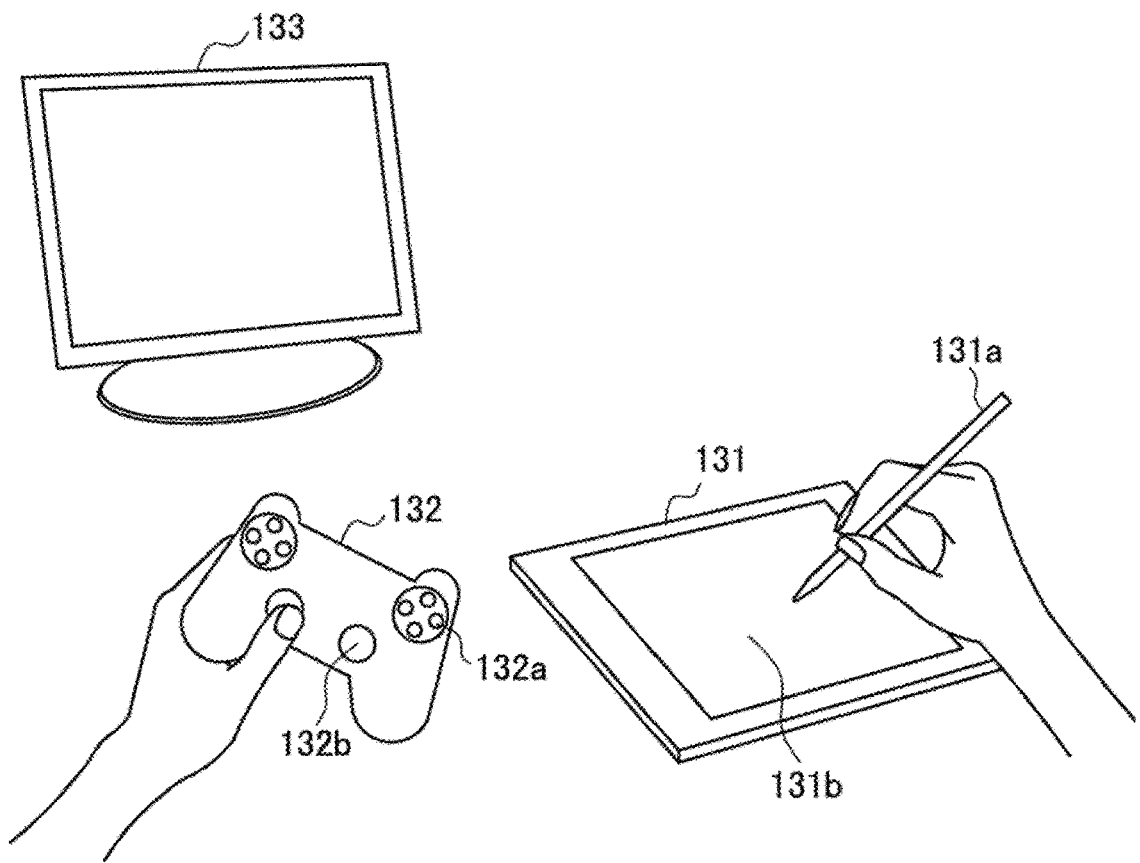
FIG. 11 is a diagram for explaining a specific example of the apparatus configuration.
Figure 12:
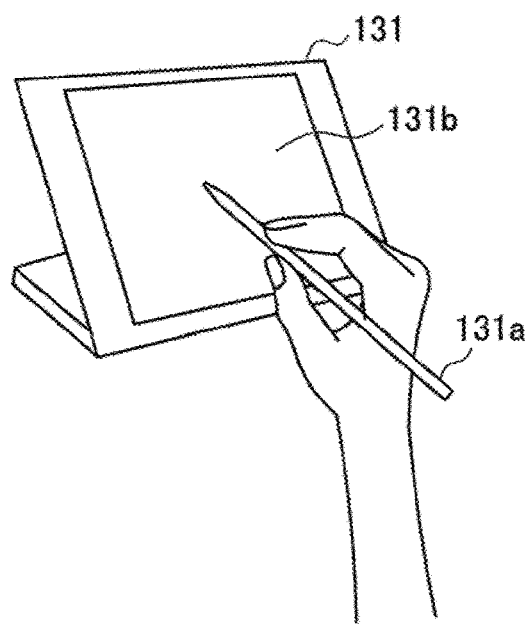
FIG. 12 is a diagram for explaining a specific example of the apparatus configuration.

In addition, the first input part 131 and the second input part 132 are not limited to those in the example in FIG. 8 above. For example, as depicted in FIG. 11, a display 133 may separately be included in addition to the first input part 131 and the second input part 132. In this case, the first image data and the like are displayed on the display 133 and the user can perform the inputting using the first input part 131 (such as, for example, the pen 131a, and the touch pad 131b executing no display) and the second input part 132 (such as, for example, a controller) watching the display. The displaying apparatus is disposed separately from the input apparatus and the user can thereby select a desired displaying apparatus (such as, for example, a displaying apparatus capable of displaying in a desired size and desired color tone, or the like), can use the existing displaying apparatus included in the working environment (such as, for example, a display disposed in a conference room, or the like), and the like. Moreover, for example, the user does not need to perform the work of drawing the annotation 10 lifting up the arm thereof toward the touch panel (that is an example of the case where the functions of a displaying apparatus and an input apparatus are realized by one apparatus) leaning on something, does not need to incline the head thereof to watch the touch panel placed flat on a desk, and the like (that is, the fatigue of the user is reduced). The work of applying the annotation 10 often takes a significantly long time and it can therefore be stated that it is especially useful that the displaying apparatus and the input apparatus are disposed separately from each other. Moreover, for example, as depicted in FIG. 12, the second input part 132 is properly not disposed and only the first input part 131 (such as, for example, the pen 131*a*, and the touch panel 131*b* available for inputting and capable of displaying) may be disposed. The user can thereby easily take out the device to be used in the work (that is the first input part 131) with the user and can therefore perform the work in various places.

Moreover, in the present embodiment, because it is assumed that the inputting relating to the annotation 10 is performed by free-hand, the first input part 131 receiving the inputting relating to the annotation 10 is more desirably operated by the dominant hand of the user (the operation is surely not limited to this). Moreover, the inputting relating to the annotation 10 may be performed using an optional method other than the free-hand (such as, for example, visual line inputting). Moreover, the setting relating to the assignment of the processes realized by the first input part 131 and the second input part 132 (such as, for example, enlarging, shrinking, a move of the visual field, or switching of the mode) may be able to be changed by the user. For example, the setting relating to the assignment of the processes realized by the buttons 132*a* and the sticks 132*b* included in the second input part 132 may be able to be changed by the user. The user can thereby perform the inputting in a desired form in accordance with the user's characteristics (such as, for example, the dominant hand, the habits, or the physical handicap).

Displaying Part 140

The displaying part 140 is configured to display thereon the first image data and the second image data on the basis of the control by the display control part 121. In the present embodiment, the displaying part 140 may be embodied by the touch panel 131*b* of the first input part 131 while the displaying part 140 is not limited to this.

Storing Part 150

The storing part 150 is configured to store therein various types of information. For example, the storing part 150 stores therein the pathological image data obtained by the image obtaining part 110, the information relating to the annotation 10 applied by the annotation processing part 122, and the like. Moreover, the storing part 150 stores therein the various types of program, the various types of parameter, and the like, that are used in the processes in the medical system 100. In addition, the pieces of information stored in the storing part 150 are not limited to the above.

The example of the configuration of the medical system 100 has been described as above. In addition, the above configuration described with reference to FIG. 2 is absolutely an example and the configuration of the medical system 100 is not limited to this example. For example, the medical system 100 may include components other than the components depicted in FIG. 2. Moreover, the configuration depicted in FIG. 2 may be embodied by any apparatus configuration. For example, the image obtaining part 110 may be embodied by a medical microscope, the first input part 131 and the displaying part 140 may be embodied by a pen-tablet, the second input part 132 may be embodied by a controller, and the control part 120 and the storing part 150 may be embodied by a server or the like, or the overall configuration may be embodied by one apparatus. Moreover, the configuration of the medical system 100 may flexibly be changed in accordance with the specification and the operation thereof.

Moreover, the function of the annotation processing part 122 or the image analyzing part 123 described above may be realized by artificial intelligence (AI) and especially by machine learning or the like. For example, the function of the annotation processing part 122 or the image analyzing part 123 can be realized on the basis of a machine learning approach such as a neural network or a regression model, or a statistical approach. More specifically, in the case of the machine learning approach, learning data tying up the image data and the annotation 10 with each other is input into a predetermined calculation model that uses a neural network or a regression model, the learning is thereby executed, and the function of the annotation processing part 122 is realized by a processing circuit that has a processing model including the produced parameters, implemented therein.

2.2. Details of Processing Relating to Annotation 10

The example of the configuration of the medical system 100 has been described above. The details of the processing relating to the annotation 10 will be described next.

Production Process for Annotation 10

Figure 13:
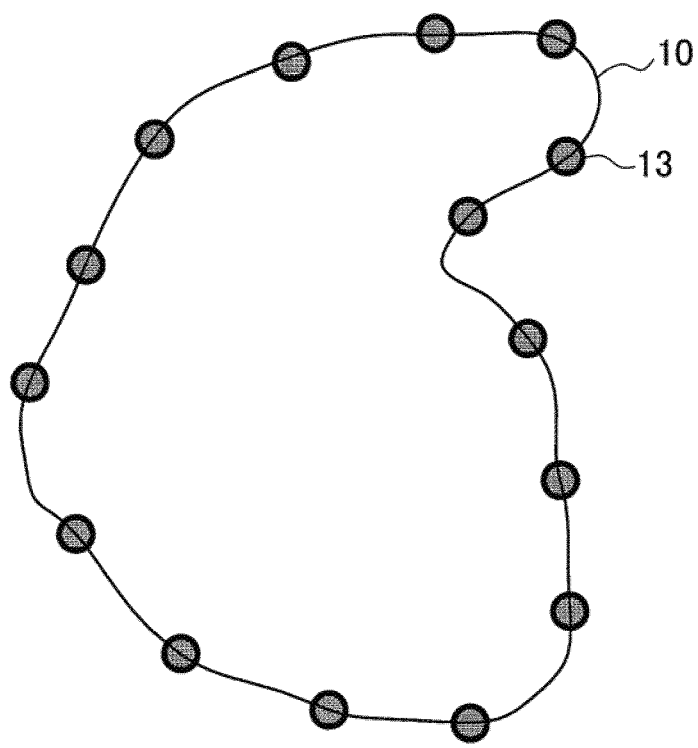
FIG. 13 is a diagram depicting an example of the annotation 10 produced by an annotation processing part 122.

A production process for the annotation 10 executed by the annotation processing part 122 will be described with reference to FIG. 13 and FIG. 14. FIG. 13 depicts an example of the annotation 10 produced by the annotation processing part 122.

As depicted in FIG. 13, the annotation processing part 122 sets the control points 13 that are the plural points on the annotation 10, and produces the annotation 10 using the control points 13. More specifically, the annotation processing part 122 sets the plural control points 13 on the annotation 10 and interpolates the control points 13 using a predetermined method.

Concerning the above, an example of the process flow relating to the production of the annotation 10 will be described with reference to FIG. 14. At step S1000 in FIG. 14, the user starts the free-hand inputting using the first input part 131. At step S1004, the annotation processing part 122 accumulates the positions in the image data for which the inputting is executed by the user, as candidate points for the control points 13.

At step S1008, the annotation processing part 122 determines whether or not the inputting by the user already comes to an end. In the case where the annotation processing part 122 determines that the inputting by the user does not yet come to an end (step S1008: No), the annotation processing part 122 continues the process at step S1004 (the accumulation process for the candidate points for the control points 13). In the case where the annotation processing part 122 determines that the inputting by the user already comes to an end (step S1008: Yes), at step S1012, the annotation processing part 122 sets the control point 13 at the position in the image data for which the inputting by the user is started (a starting point).

At step S1016, the annotation processing part 122 thereafter sets the control points 13 at the candidate points at predetermined distance intervals on the basis of the control point 13 that is set to be the starting point. At step S1020, the annotation processing part 122 determines whether or not the control points 13 are set to the position in the image data for which the inputting by the user comes to an end (the ending point). In the case where the annotation processing part 122 determines that the control points 13 are not set to the end point (step S1020: No), the annotation processing part 122 continues the process at step S1016 (the setting process for the control points 13). In the case where the annotation processing part 122 determines that the control points 13 are set to the ending point (step S1020: Yes), at step S1024, the annotation processing part 122 interpolates the control points 13 using a predetermined method, and thereby causes the series of annotation 10 production process steps to come to an end.

Figure 14:
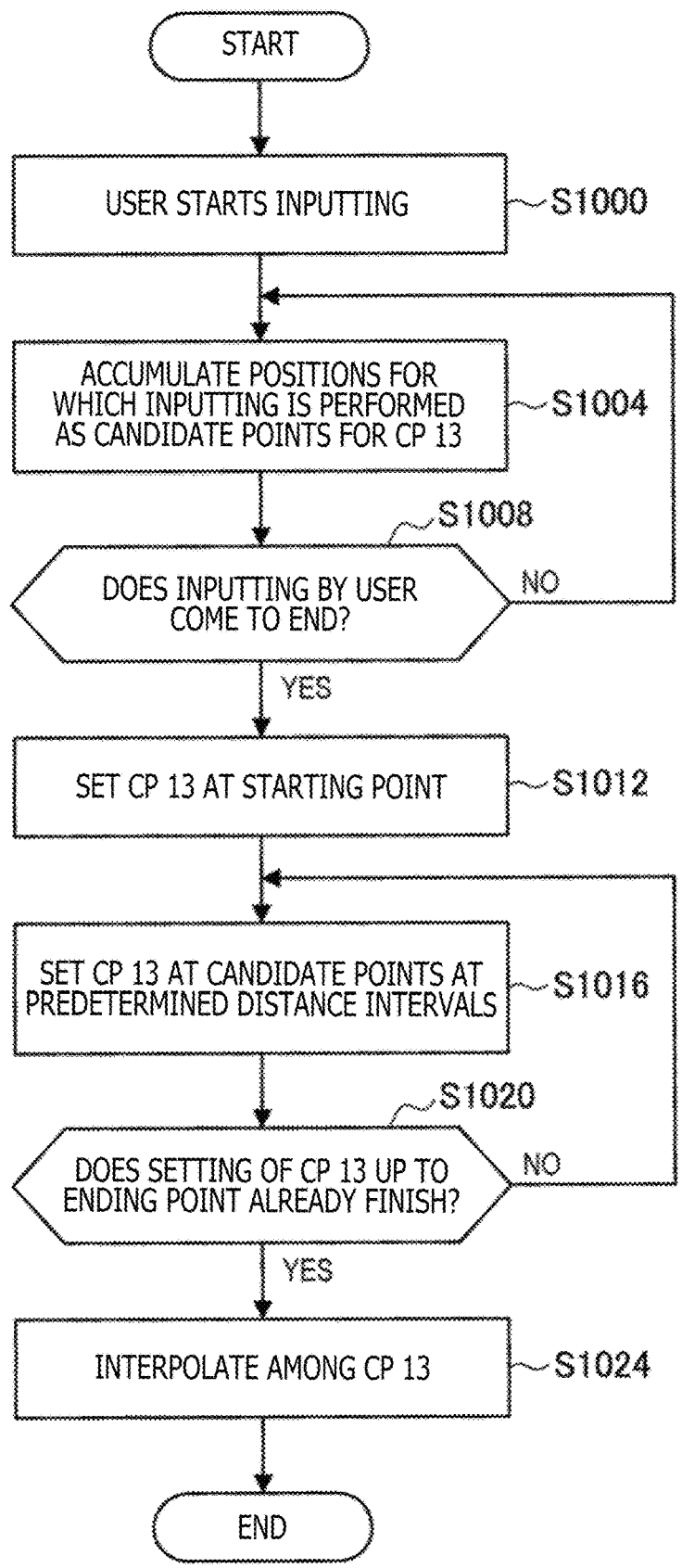
FIG. 14 is a flowchart depicting an example of a process flow relating to the production of the annotation 10.

In addition, the control points 13 are set and interpolated after the inputting by the user comes to an end in the example of the process flow in FIG. 14 while the control points 13 may sequentially be set and interpolated even in the course of performing the inputting by the user.

Concerning the above, it is assumed that the method for the interpolation executed at step S1024 is spline interpolation. More specifically, the annotation processing part 122 executes the spline interpolation such that the intervals of the control points 13 are constituted by five lines (the five lines connecting four interpolation points). It is assumed as above that the inputting relating to the annotation 10 is performed freehand while the annotation processing part 122 produces the annotation 10 using the spline interpolation and can thereby prevent the annotation 10 from being warped by the free-hand inputting (in other words, the shape of the annotation 10 can be set to be smoother). Moreover, the number of interpolation points used in the spline interpolation is not especially limited, and may flexibly be designed in accordance with the conditions such as the required smoothness of the annotation 10 and the permissible amount of the calculation. Moreover, any method for interpolation other than the spline interpolation (such as, for example, linear interpolation) may be used.

Moreover, the "predetermined distance interval" used in the process at step S1016 (in other words, the intervals each between the control points 13) is determined in accordance with the resolution of the image data that the user watches to apply more accurate annotation 10, that is, the second resolution (or the magnification). More specifically, the "predetermined distance interval" becomes smaller as the second resolution becomes higher, and becomes larger as the second resolution becomes lower. The control points 13 are thereby more densely set in the case where the user sets the second resolution to be higher for the user to apply the annotation 10 to a smaller observation target object and, in contrast, the control points 13 are thereby more roughly set in the case where the user sets the second resolution to be lower for the user to apply the annotation 10 to a larger observation target object. In other words, the optimal control points 13 are thereby set in accordance with the dimension of the annotation 10 that the user desires to apply and the production of a more accurate annotation 10 is therefore enabled. In addition, the smallest value of the "predetermined distance interval" (in other words, the intervals each between the control points 13) (in other words, the case where the second resolution (or the magnification) is the highest) is desirably equal to or smaller than the dimension of the cell (such as, for example, approximately 10 [μm]) (and is surely not limited to this).

Moreover, one characteristic of the pathological image data is that this data has a large number of pixels while, when a relatively large annotation 10 is applied to the pathological image data because of the large number of pixels, the number of the control points 13 is increased and an increase of the computation amount due to this may degrade the drawing performance. Concerning this, the annotation processing part 122 can optimize the number of the control points 13 by determining the intervals among the control points 13 in accordance with the second resolution (or the magnification) as above, and can therefore suppress any increase of the computation amount and can improve the drawing performance. In addition, the annotation processing part 122 draws the annotation 10 at a high frame rate such that the displaying of the image data is smoothly executed even at a higher resolution.

Correction Process for Annotation 10

A correction process for the annotation 10 executed by the annotation processing part 122 will be described next with reference to FIG. 15 to FIG. 23. For example, in the case where the annotation 10 is applied by machine learning of where the annotation 10 is applied using the first image data, the annotation processing part 122 can correct the annotation 10 further using the second image data (the correction surely does not necessarily need to be executed using the second image data). The annotation processing part 122 corrects the annotation 10 using the control points 13 on the basis of the inputting by the user.

Figure 15:
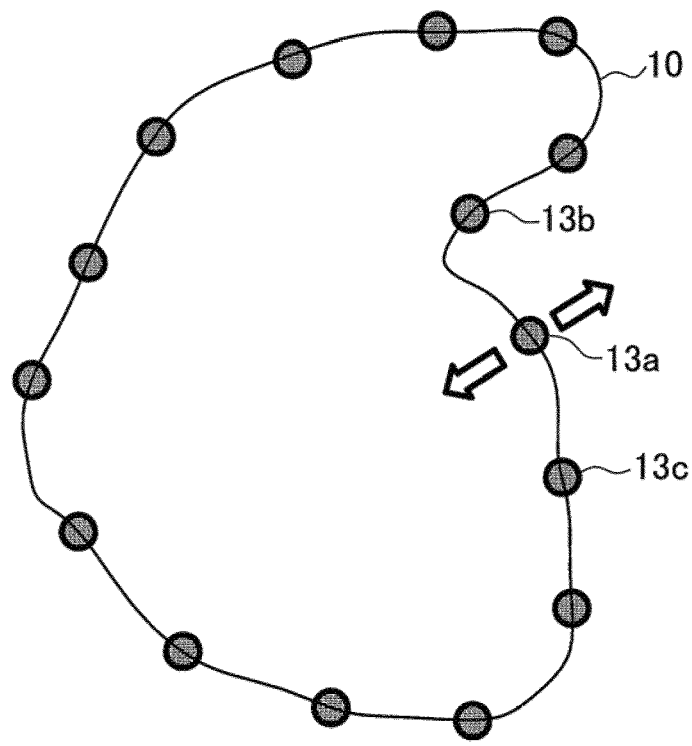
FIG. 15 is a diagram for explaining correction of the annotation 10 executed by moving a control point 13.
Figure 16:
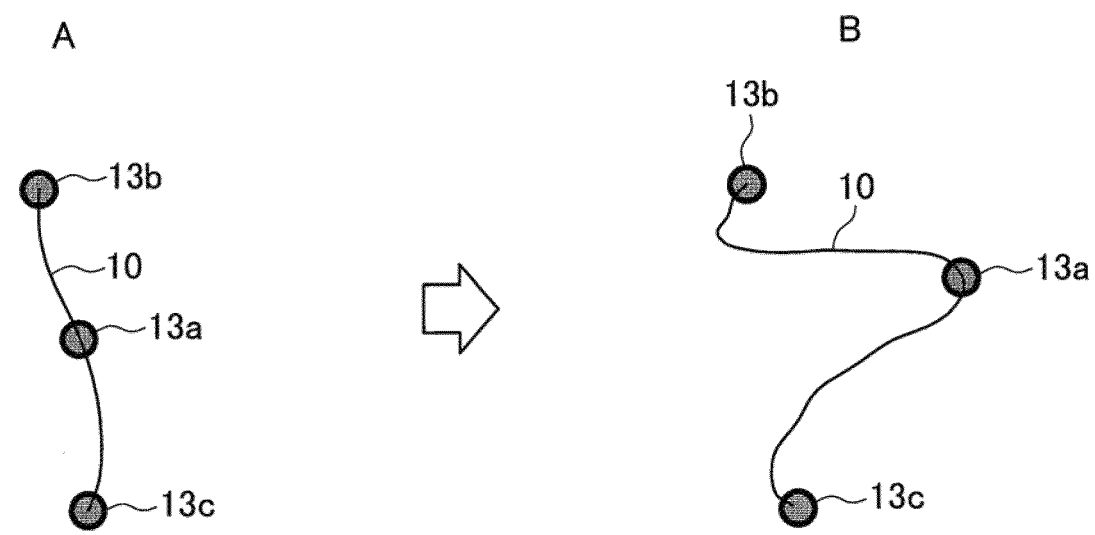
FIG. 16 is a diagram for explaining the correction of the annotation 10 executed by moving the control point 13.

For example, in the case where the annotation 10 as depicted in FIG. 15 is produced, the user can correct the annotation 10 by moving the positions of the control points 13 included in the annotation 10, using a predetermined method. More specifically, the user may correct the annotation 10 depicted in A of FIG. 16, by dragging a control point 13a included therein, to the annotation 10 depicted in B of FIG. 16. The user can thereby intuitively perform especially fine correction.

Figure 17:
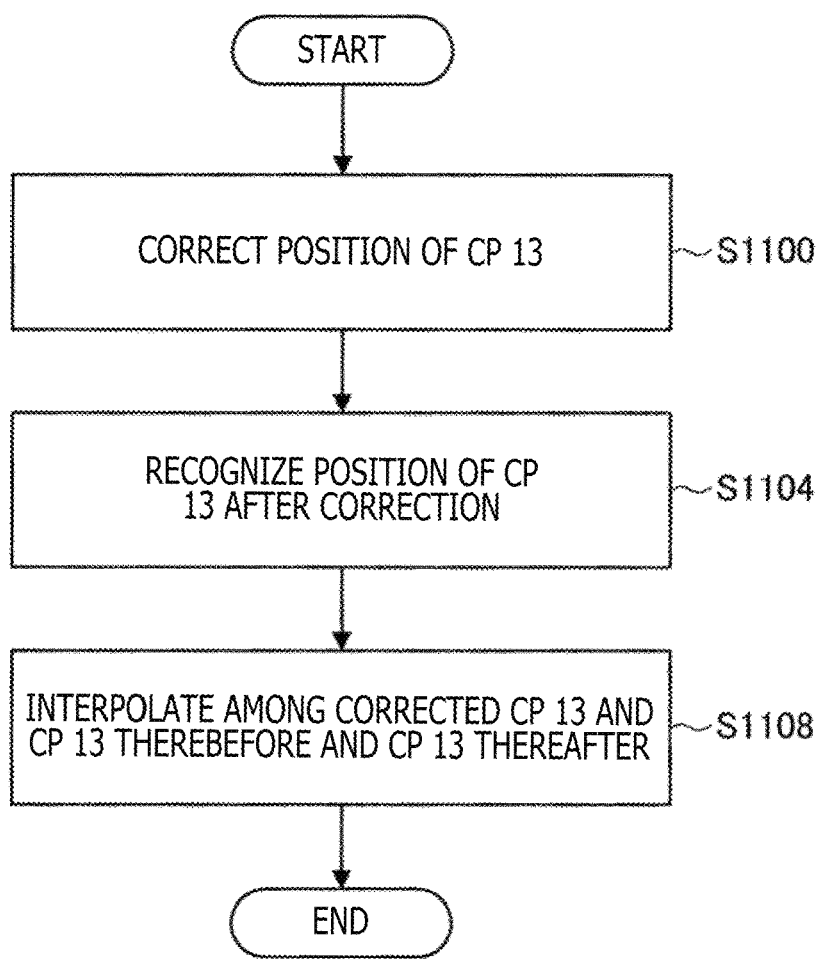
FIG. 17 is a flowchart depicting an example of a process flow relating to the correction of the annotation 10 executed by moving the control point 13.

FIG. 17 is a diagram depicting an example of the process flow relating to the correction (the correction executed by the move of the control point 13). At step S1100, the user corrects the position of the control point 13 included in the annotation 10 using a predetermined method (such as, for example, dragging). At step S1104, the annotation processing part 122 recognizes the position of the control point 13 after the correction (the position in the image data). At step S1108, the annotation processing part 122 interpolates the intervals between the control point 13 at the corrected position, and the control points 13 therebefore and thereafter using a predetermined method (such as, for example, the spline interpolation) and thereby causes the series of annotation 10 correction process steps to come to an end.

Moreover, the annotation processing part 122 may correct the first annotation 10 applied first, using the second control point 15 included in a second annotation 14 applied later. At this time, the annotation processing part 122 determines the correction range of the first annotation 10 on the basis of the relative positional relation between the first control point 13 included in the first annotation 10 and the second control point 15 included in the second annotation 14.

Figure 18:
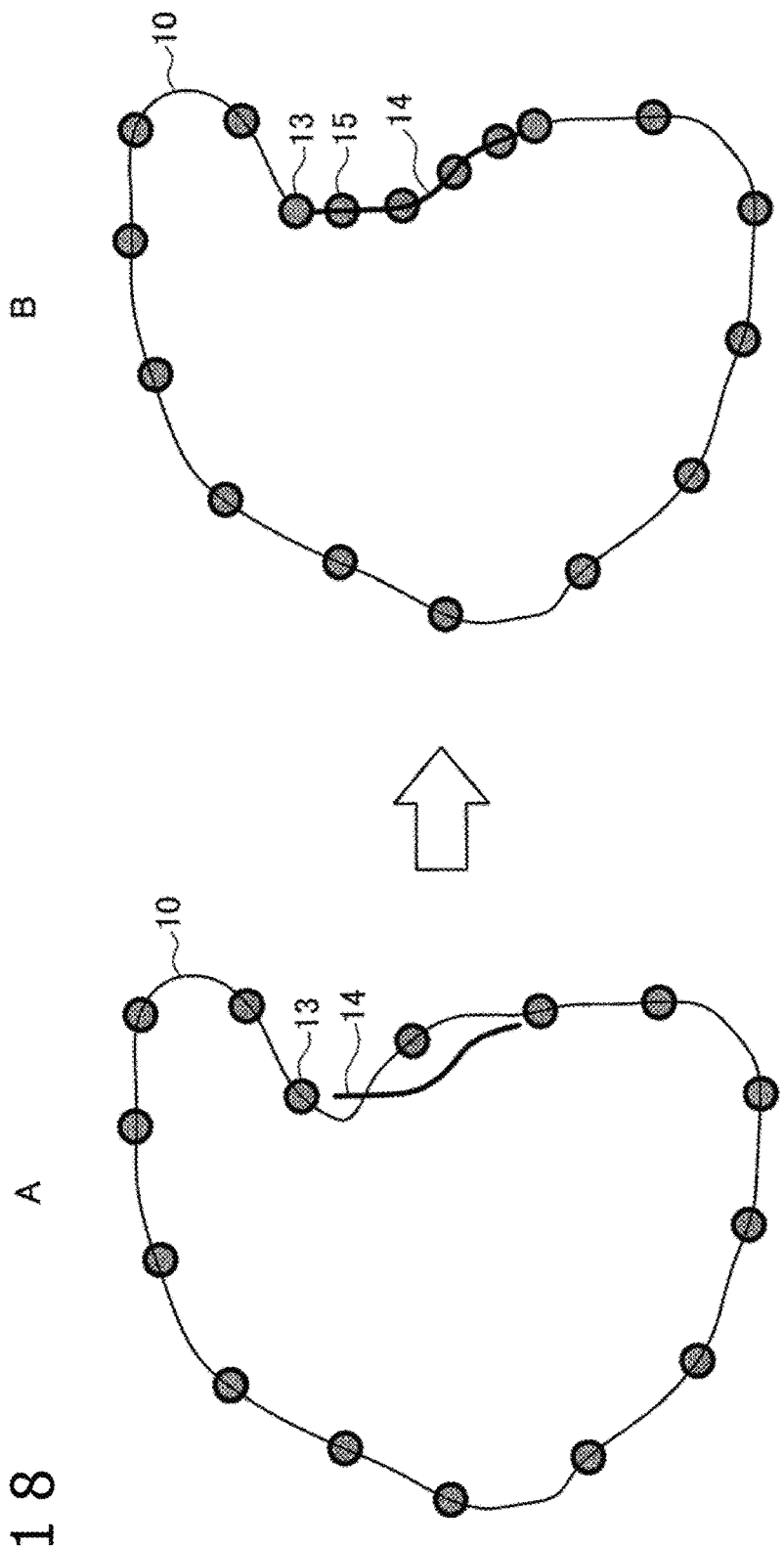
FIG. 18 is a diagram for explaining the correction of the first annotation 10 using a second annotation 14.

For example, in the case where the first annotation 10 as depicted in A of FIG. 18 is already produced, the user newly draws the second annotation 14 for correction (as depicted in A of FIG. 18, the second annotation 14 is a free line that is not closed). The annotation processing part 122 thereafter sets the second control point 15 on the second annotation 14 using the method described with reference to FIG. 14. As depicted in B of FIG. 18, the annotation processing part 122 thereafter connects the second control points 15 included in the second annotation 14 on both ends thereof to any one of the first control points 13 included in the first annotation 10.

More specifically, the annotation processing part 122 connects the second control points 15 included in the second annotation 14 on both ends thereof to the first control point 13 whose offset distance to each of the second control points 15 is smallest. The annotation processing part 122 thereafter deletes the first annotation 10 that corresponds to the section of the second annotation 14 and thereby corrects the first annotation 10. In addition, in the example in B of FIG. 18, because the user draws the second annotation 14 at a resolution higher than that of the time when the first annotation 10 is produced, the intervals among the second control points 15 are each smaller than each of the intervals among the first control points 13.

The user can correct the annotation 10 by the intuitive inputting that is the redrawing of the more accurate annotation 10, by using the method described with reference to FIG. 18. Moreover, in the correction described with reference to FIG. 15 to FIG. 17 (the correction by the move of the control point 13), the user is required to move the positions of all the control points 13 in the correction range. Moreover, in the case where the position of only one control point 13 is moved, or the like, the user may be unable to perform any correction intended by the user by abrupt turning of the annotation 10. On the other hand, the method described with reference to FIG. 18 can address this problem and can more properly realize the correction for the annotation 10.

Figure 19:
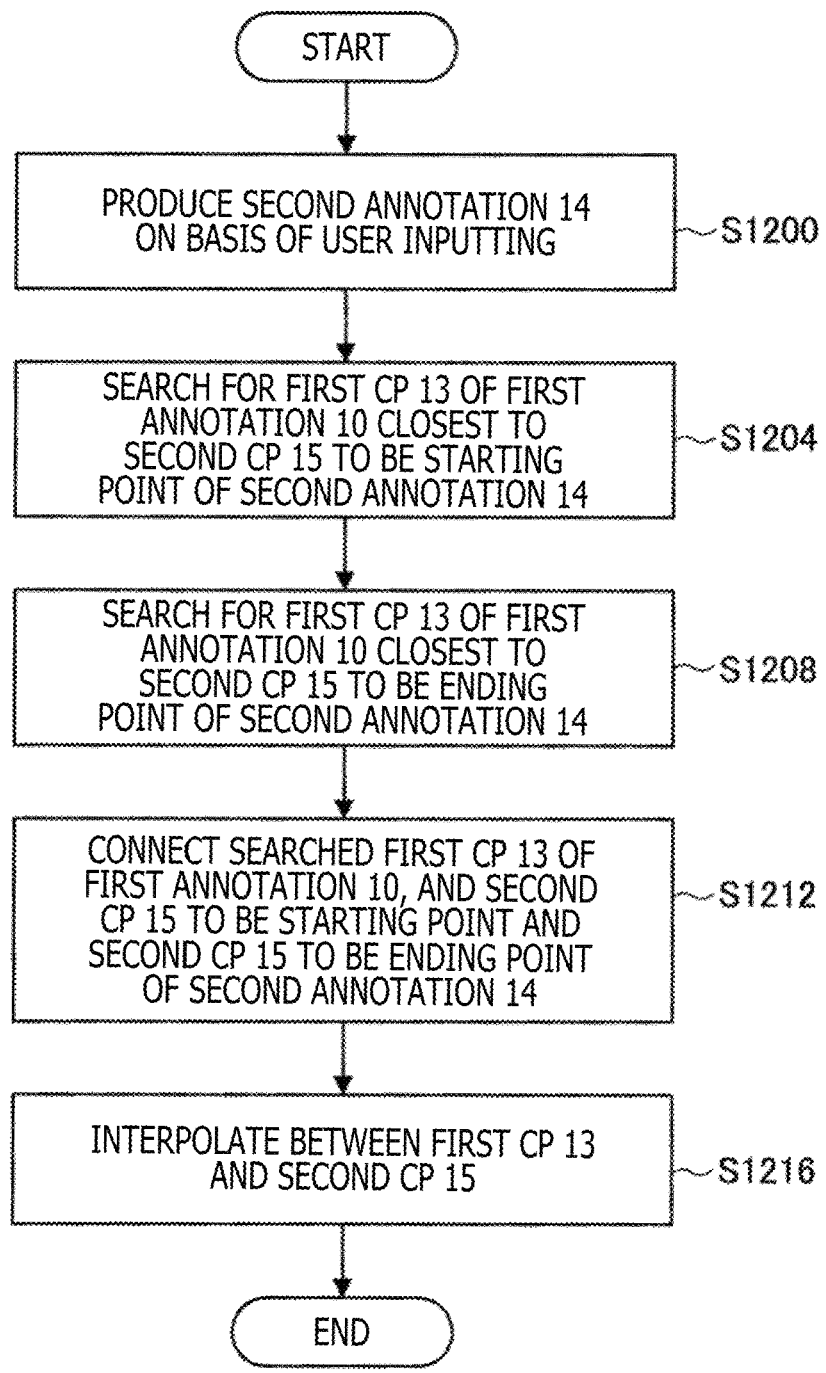
FIG. 19 is a flowchart depicting an example of the process flow relating to the correction of the first annotation 10 using the second annotation 14.

FIG. 19 is a diagram depicting an example of the process flow relating to the correction (the correction using the second annotation 14). At step S1200, the annotation processing part 122 produces the second annotation 14 on the basis of the inputting by the user. At step S1204, the annotation processing part 122 searches for the first control point 13 included in the first annotation 10 that is closest to the second control point 15 to be the starting point of the second annotation 14. At step S1208, the annotation processing part 122 searches for the first control point 13 included in the first annotation 10 that is closest to the second control point 15 to be the ending point of the second annotation 14.

At step S1212, the annotation processing part 122 connects the searched first control point 13 included in the first annotation 10 to each of the second control point 15 to be the starting point and the second control point 15 to be the ending point of the second annotation 14. At this time, the annotation processing part 122 deletes the first annotation 10 that corresponds to the section of the second annotation 14. At step S1216, the annotation processing part 122 interpolates the first control point 13 and the second control point 15 connected to each other, using a predetermined method (such as, for example, the spline interpolation), and thereby causes the series of annotation 10 correction process steps to come to an end.

In addition, in the method described with reference to FIG. 18 and FIG. 19, the annotation processing part 122 determines whether the annotation processing part 122 executes the correction for the annotation 10 or executes new production of the annotation 10, on the basis of the offset distance between the second control point 15 to be the starting point of the second annotation 14 and the first control point 13 that is closest thereto. More specifically, in the case where the offset distance between the second control point 15 to be the starting point of the second annotation 14 and the first control point 13 that is closest thereto is smaller than a predetermined value, the annotation processing part 122 executes the correction for the annotation 10 and, in contrast, in the case where the offset distance is equal to or larger than the predetermined value, the annotation processing part 122 executes the new production of the annotation 10. The user thereby does not need to designate the inputting relating to the correction or the inputting relating the new production (the user may surely perform these designations). In addition, as above, the intervals among the control points 13 are determined in accordance with the second resolution (or the magnification) while the above "predetermined value" used in the determination for the correction or the new production may also be determined in accordance with the second resolution (or the magnification) and the "predetermined value" may be a value that is, for example, close to the interval between the control points 13. The "predetermined value" is thereby optimized in accordance with the second resolution (or the magnification) and the user can therefore more easily perform the inputting relating to the annotation 10. As above, the minimal value of the interval between the control points 13 (in other words, in the case where the second resolution (or the magnification) is the highest), is desirably equal to or smaller than the dimension of the cell (such as, for example, approximately 10 [μm]) while this also applied to the minimal value of the "predetermined value" (the minimal value is surely not limited to this). Moreover, the annotation processing part 122 may notify the user as to whether the annotation processing part 122 corrects the annotation 10 or newly produces an annotation 10, using a method such as: changing the color, the line type (such as, for example, a dotted line or a solid line), the line width, or the like; changing the type of the cursor 12; or the like.

Moreover, in the method described with reference to FIG. 18 and FIG. 19, the annotation processing part 122 may not connect the first control point 13 and the second control point 15 to each other but may connect the interpolation point of the spline interpolation and the second control point 15 to each other. More specifically, in the case where the spline interpolation is employed as the interpolation method, the annotation processing part 122 may use the interpolation point of the spline interpolation, in the processing as the control point 13. The interpolation point of the spline interpolation is handled as the control point 13 and the annotation processing part 122 can thereby execute more detailed correction. Moreover, the connection and the interpolation are executed for the first control point 13 and the second control point 15 after the second annotation 14 is drawn on the basis of the inputting by the user in the example of the process flow in FIG. 19 while the connection and the interpolation may sequentially be executed for the first control point 13 and the second control point 15 by the fact that the second control points 15 are sequentially produced even in the course of the drawing of the second annotation 14.

Moreover, the annotation processing part 122 may change the first control point 13 to be the connection target, on the basis of the angle whose vertex is either one of the first control point 13 and the second control point 15 that are connected to each other.

Figure 20:
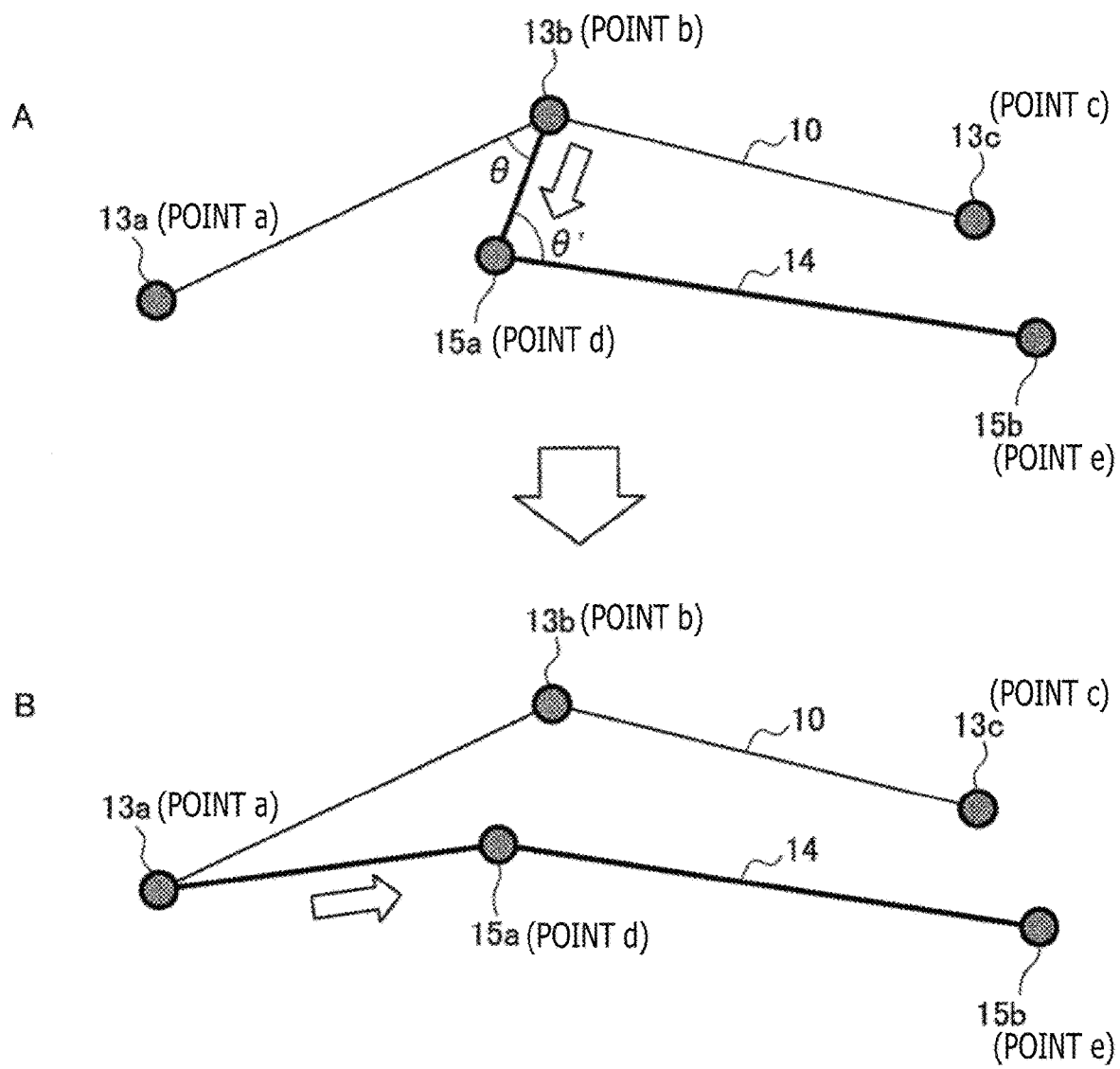
FIG. 20 is a diagram for explaining a change of the first control point 13 to be a target of connection with a second control point 15.

For example, it is assumed that the first annotation 10 as depicted in A of FIG. 20 is produced, the correction using the second annotation 14 is thereafter executed, and thereby a first control point 13b and a second control point 15a are connected to each other. In this case, when the first control point 13b and the second control point 15a are only simply connected to each other, an abrupt variation is generated by the fact that an angle θ whose vertex is the first control point 13b and an angle θ' whose vertex is the second control point 15a are each smaller than 90° and any correction intended by the user may therefore be unable to be executed.

In this case, the annotation processing part 122 calculates whether or not the angle θ and the angle θ' are each smaller than a predetermined value (such as, for example, 90°) and, when the annotation processing part 122 determines that the angle θ and the angle θ' are each smaller than the predetermined value, the annotation processing part 122 changes, for example, as depicted in B of FIG. 20, the first control point 13 to be the connection target, to the first control point 13a that is before by one and that is adjacent to the first control point 13b. In addition, though not depicted in B of FIG. 20, the annotation processing part 122 also executes similar process for the other end of the second annotation 14. The annotation processing part 122 can thereby prevent generation of any abrupt variation due to the correction and can therefore execute the correction in accordance with the intention of the user.

In addition, the calculation method for the angle θ and the angle θ' is not especially limited. For example, the annotation processing part 122 may manage the vector extending between the control points 13 and may calculate the angle θ and the angle θ' by calculating the inner product of the vectors or the like.

Moreover, the case where the predetermined value is 90° has been described as an example in the above while the predetermined value is not especially limited and may flexibly be varied in accordance with the precision required to the annotation 10, the observation target object, and the like. Moreover, the case where both the angle θ and the angle θ' are to be determined has been described as an example in the above while either one of the angle θ and the angle θ' may be the target of the determination. Moreover, the case where the first control point 13 to be connected is changed to the first control point 13 before by one and adjacent to the first control point 13 has been described as an example in the above while the first control point 13 to be connected may be changed to the first control point 13 before by two or more the first control point 13.

Figure 21:
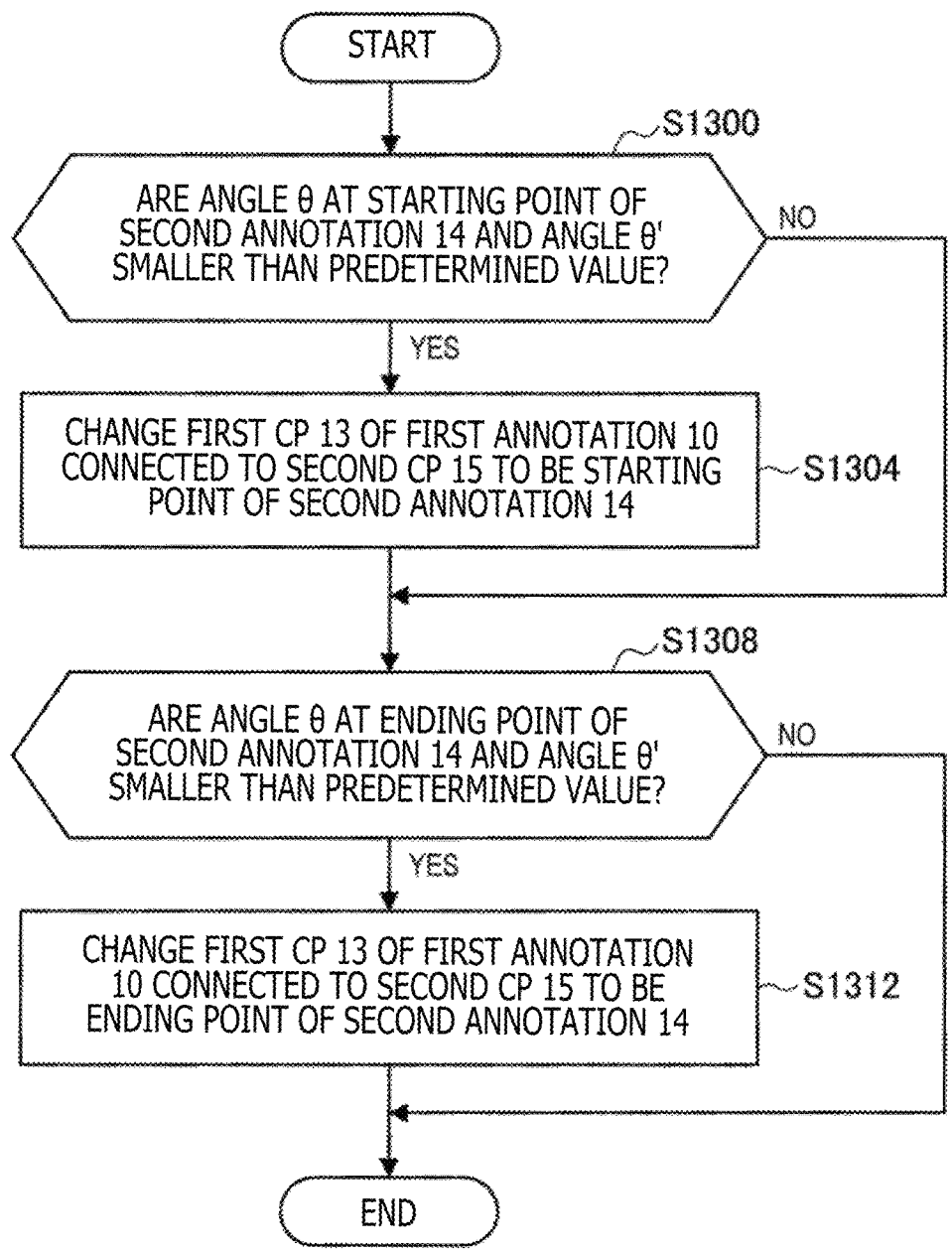
FIG. 21 is a flowchart depicting an example of the process flow relating to the change of the first control point 13 to be the target of the connection with the second control point 15.

FIG. 21 is a diagram depicting an example of the process flow relating to the change of the first control point 13 to be connected. It is assumed that, before the process in FIG. 21 is executed, the connection of the first annotation 10 and the second annotation 14 to each other is executed in the process in FIG. 19.

At step S1300, the annotation processing part 122 calculates whether or not the angle θ and the angle θ' at the starting point of the second annotation 14 are each smaller than a predetermined value. In the case where the annotation processing part 122 determines that the angle θ and the angle θ' at the starting point of the second annotation 14 are each smaller than the predetermined value (step S1300: Yes), at step S1304, the annotation processing part 122 changes the first control point 13 included in the first annotation 10, connected to the second control point 15 to be the starting point of the second annotation 14. In the case where the annotation processing part 122 determines that the angle θ and the angle θ' at the starting point of the second annotation 14 are each equal to or larger than the predetermined value (step S1300: No), the annotation processing part 122 does not change the first control point 13 to be connected.

At step S1308, the annotation processing part 122 calculates whether or not the angle θ and the angle θ' at the ending point of the second annotation 14 are each smaller than a predetermined value. In the case where the annotation processing part 122 determines that the angle θ and the angle θ' at the ending point of the second annotation 14 are each smaller than the predetermined value (step S1308: Yes), at step S1312, the annotation processing part 122 changes the first control point 13 included in the first annotation 10, connected to the second control point 15 to be the ending point of the second annotation 14 and thereby causes the series of process steps to come to an end. In the case where the annotation processing part 122 determines that the angle θ and the angle θ' at the ending point of the second annotation 14 are each equal to or larger than the predetermined value (step S1308: No), the annotation processing part 122 causes the series of process steps to come to an end without changing the first control point 13 to be connected.

Figure 22:
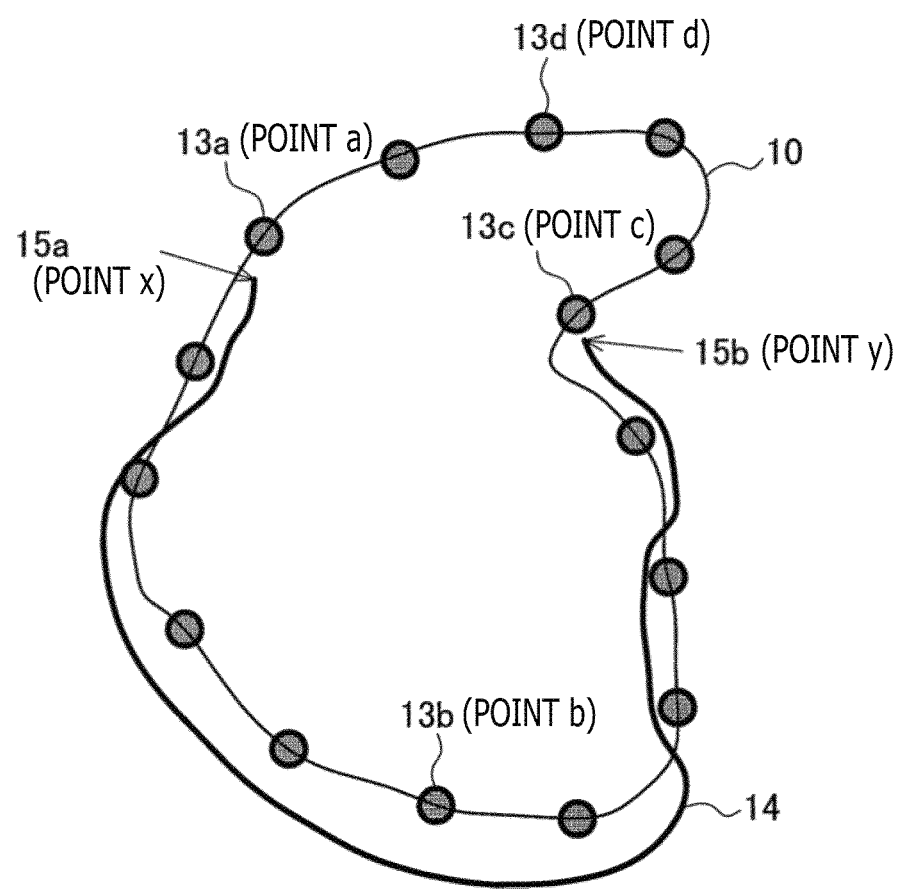
FIG. 22 is a diagram for explaining a determination method for a correction range of the first annotation 10.

Concerning the above, it is assumed that a second annotation 14 starting from a point x and reaching to a point y is drawn in the situation where the first annotation 10 as depicted in FIG. 22 is already produced. In this case, the annotation processing part 122 needs to determine which one of the range connecting a point a to a point b to a point c and the range connecting the point a to a point d to a point c of the first annotation 10 is the correction range.

In this case, as above, the annotation processing part 122 also determines the correction range of the first annotation 10 on the basis of the relative positional relation between the first control point 13 included in the first annotation 10 and the second control point 15 included in the second annotation 14. For example, the annotation processing part 122 searches for the first control point 13 closest to each of the second control points 15 included in the second annotation 14, and checks whether the closest first control point 13 belongs to which one of the range connecting the point a to the point b to the point c and the range connecting the point a to the point d to the point c. The annotation processing part 122 thereafter determines that a range to which more first control points 13 closest to each of the second control points 15 belong, to be the correction range.

In the example in FIG. 22, the range to which more first control points 13 closest to the second control points 15 belong is the range that connects the point a to the point b to the point c, and the annotation processing part 122 therefore determines that the range connecting the point a to the point b to the point c is the correction range, and corrects the first annotation 10 by connecting the point a to the point x to the point y to the point c to the point d to the point a. The annotation processing part 122 can thereby properly realize the correction intended by the user. In addition, the second control point 15a and the second control point 15b in FIG. 22 are excluded from the targets of the above processing.

Figure 23:
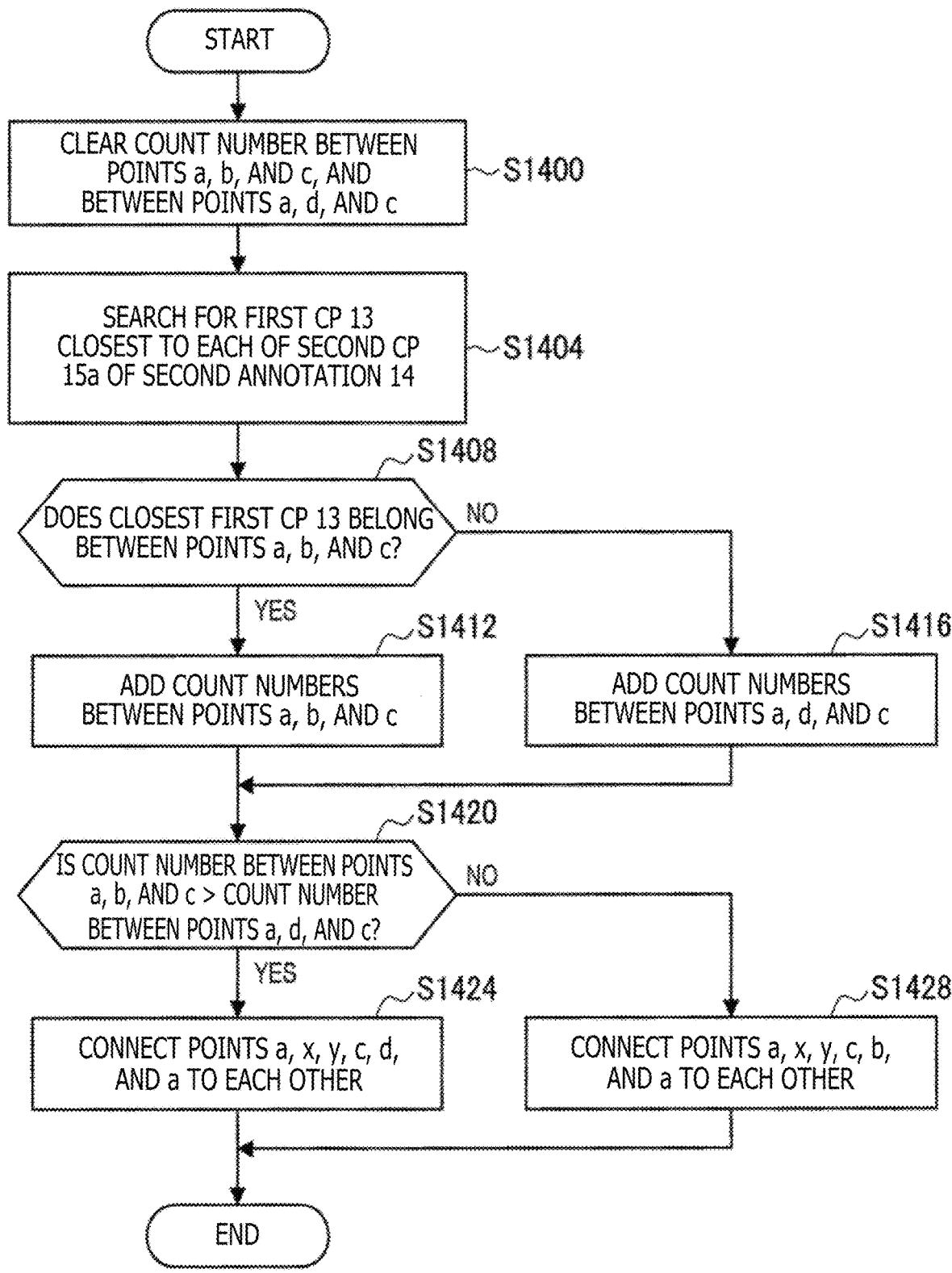
FIG. 23 is a flowchart depicting an example of the process flow relating to the determination of the correction range of the first annotation 10.

FIG. 23 is a diagram depicting an example of the process flow relating to the determination of the correction range. At step S1400, the annotation processing part 122 clears the count number for each of the range connecting the point a to the point b to the point c and the range connecting the point a to a point d to a point c. At step S1404, the annotation processing part 122 searches for the first control point 13 closest to each of the second control points 15 included in the second annotation 14.

In the case where the closest first control point 13 belongs to the range connecting the point a to the point b to the point c (step S1408: Yes), at step S1412, the annotation processing part 122 adds the count number of the range connecting the point a to the point b to the point c. On the other hand, the closest first control point 13 belongs to the range connecting the point a to the point d to the point c (step S1408: No), at step S1416, the annotation processing part 122 adds the count number of the range connecting the point a to the point d to the point c.

In the case where the count number of the range connecting the point a to the point b to the point c exceeds the count number of the range connecting the point a to the point d to the point c (step S1420: Yes), at step S1424, the annotation processing part 122 determines that the range connecting the point a to the point b to the point c is the correction range, corrects the first annotation 10 by connecting the point a to the point x to the point y to the point c to the point d to the point a, and causes the series of process steps to come to an end. On the other hand, in the case where the count number of the range connecting the point a to the point b to the point c is equal to or smaller than the count number of the range connecting the point a to the point d to the point c (step S1420: No), at step S1428, the annotation processing part 122 determines that the range connecting the point a to the point d to the point c is the correction range, corrects the first annotation 10 by connecting the point a to the point x to the point y to the point c to the point b to the point a, and causes the series of process steps to come to an end.

In addition, when the counting is executed at step S1408 to step S1416, the annotation processing part 122 may execute weighting in accordance with the offset distance between the second control point 15 and the closest first control point 13. The annotation processing part 122 can thereby improve the correction precision of the first annotation 10.

2.3. Hardware Configuration

The details of the processes relating to the annotation 10 has been described in the above. An example of the hardware configuration of an information processing apparatus 900 that realizes the various types of function of the medical system 100 will be described next with reference to FIG. 24.

Figure 24:
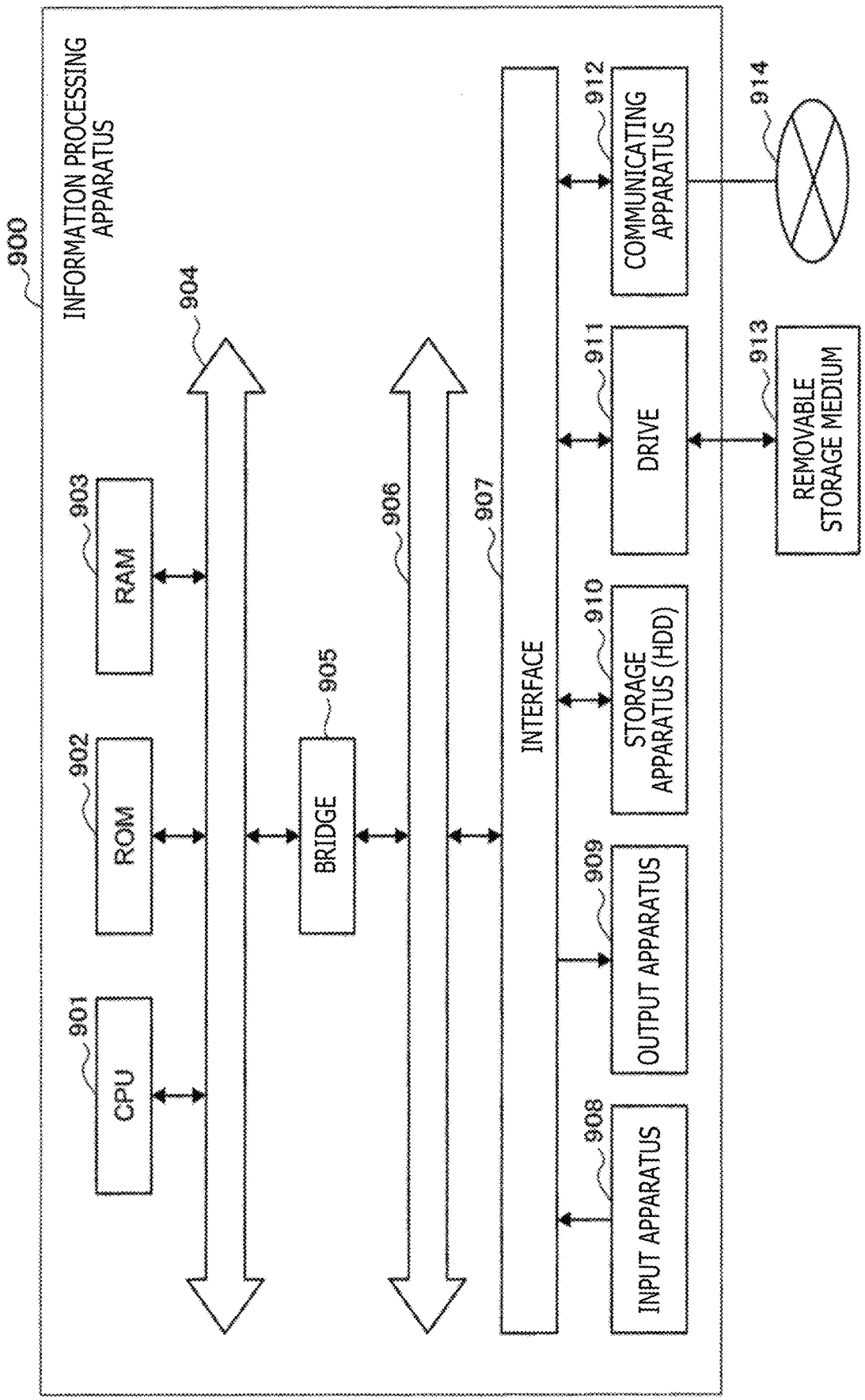
FIG. 24 is a block diagram depicting an example of the hardware configuration of an information processing apparatus 900 that realizes various types of function of a medical system 100.

FIG. 24 is a diagram depicting a hardware configuration of the information processing apparatus 900. The information processing apparatus 900 includes a CPU (Central Processing Unit) 901, a ROM (Read Only Memory) 902, a RAM (Random Access Memory) 903, a host bus 904, a bridge 905, an external bus 906, an interface 907, an input apparatus 908, an output apparatus 909, a storage apparatus (HDD) 910, a drive 911, and a communicating apparatus 912.

The CPU 901 functions as a computation processing apparatus and a control apparatus, and controls the overall operations of the information processing apparatus 900 in accordance with various types of program. Moreover, the CPU 901 may be a microprocessor. The ROM 902 stores therein the program, the computation parameters, and the like that are used by the CPU 901. The RAM 903 temporarily stores therein the programs used in the execution by the CPU 901, the parameters properly varied in the execution thereof, and the like. These components are connected to each other by a host bus 904 that includes a CPU bus and the like. A partial function of the control part 120 or the image obtaining part 110 of the medical system 100 may be realized by the CPU 901, the ROM 902, and the RAM 903 in cooperation with each other.

The host bus 904 is connected to the external bus 906 such as a PCI (Peripheral Component Interconnect/Interface) through the bridge 905. In addition, the host bus 904, the bridge 905, and the external bus 906 do not necessarily need to each be separately configured, and these functions may be implemented in one bus.

The input apparatus 908 includes: input means for a user to input information such as a mouse, a keyboard, a touch panel, buttons, a microphone, a switch, a lever, or a camera; an input control circuit that produces an input signal on the basis of inputting by the user and that outputs the input signal to the CPU 901 and the like. The user of the information processing apparatus 900 can input various types of information into the apparatuses, can instruct process operations to the apparatuses, and the like by operating the input apparatus 908. A partial function of the input part 130 or the image obtaining part 110 of the medical system 100 is realized by the input apparatus 908.

The output apparatus 909 includes a displaying apparatus such as, for example, a CRT (Cathode Ray Tube) display apparatus, a liquid crystal display (LCD) apparatus, an OLED (Organic Light Emitting Diode) apparatus, or a lamp. Furthermore, the output apparatus 909 includes a sound output apparatus such as a speaker, a headphone, and the like. The displaying apparatus displays thereon various types of information such as the image data using a text or an image. On the other hand, the sound output apparatus converts sound data and the like into sounds and outputs the sounds. The function of the displaying part 140 of the medical system 100 is realized by the output apparatus 909.

The storage apparatus 910 is an apparatus for storing data. The storage apparatus 910 may include a storage medium, a recording apparatus that records data on the storage medium, a reading apparatus that reads data from the storage medium, and a deleting apparatus that deletes data recorded on the storage medium. The storage apparatus 910 includes, for example, an HDD (Hard Disk Drive). The storage apparatus 910 drives the hard disk, and stores therein the programs to be executed by the CPU 901 and various types of data. The function of the storing part 150 of the medical system 100 is realized by the storage apparatus 910.

The drive 911 is a reader/writer for the storage medium, and is incorporated in or externally attached to the information processing apparatus 900. The drive 911 reads information recorded on a removable storage medium 913 such as a magnetic disc, an optical disc, a magnetooptical disc, or a semiconductor memory, that is attached thereto, and outputs the information to the RAM 903. Moreover, the drive 911 also can write information into the removable storage medium 913.

The communicating apparatus 912 is, for example, a communication interface that includes a communicating device or the like to connect the information processing apparatus 900 to a communication network 914.

2.4. Variations of System Configuration

The example of the hardware configuration of the information processing apparatus 900 that realizes the various types of function of the medical system 100 has been described in the above. Variations of the configuration of the medical system 100 according to the present embodiment will be described next.

The medical system 100 according to the present embodiment can be realized by each of various configurations. For example, the medical system 100 or a medical apparatus according to the present embodiment may include an imaging apparatus that produces the pathological image data (including, for example, a scanner or an imaging device) and an information processing apparatus that executes processes for the pathological image data. In this case, the image obtaining part 110 depicted in FIG. 2 can be realized by the imaging apparatus and the other configurations can be realized by the information processing apparatus.

Moreover, the medical system 100 (or medical apparatus) according to the present embodiment may include an imaging apparatus that produces the pathological image data (including, for example, a scanner or an imaging device) and software that is used in the processes for the pathological image data. In other words, any physical configuration that stores therein the software, that executes the software, and the like (such as, for example, a memory or a processor) may not be included in the medical system 100. In this case, the image obtaining part 110 depicted in FIG. 2 can be realized by an imaging apparatus and the other configurations can be realized by an information processing apparatus that executes the software. The software thereafter is provided to the information processing apparatus through a network (from, for example, a website or a cloud server), is provided to the information processing apparatus through any optional storage medium (such as, for example, a disk), or the like. Moreover, the information processing apparatus that executes the software may be any one of various types of server (such as, for example, a cloud server), a general-purpose computer, a PC, or a tablet PC. In addition, the method of providing the software to the information processing apparatus and the type of the information processing apparatus are not limited to the above. Moreover, the configuration of the medical system 100 according to the present embodiment is not necessarily limited to the above and it should be noted that any configuration that the what-is-called those skilled in the art can conceive on the basis of the technical level at the time of the use may be applied.

3. Conclusion

As has been described above, the medical system 100 according to the present disclosure: for the pathological image data that is produced by imaging one observation target object and that includes first and second image data, the second image data relating to the observation target object but being different to the first image data, can cause the displaying part 140 to display thereon the first image data and the second image data; and can apply the annotation 10 to each of the first image data and the second image data on the basis of the inputting by the user. The user can thereby execute the inputting relating to the annotation 10 watching both the first image data and the second image data where the second image data relates to the observation target object but is different to the first image data and the present disclosure can therefore more properly apply the annotation 10 to the pathological image data.

Moreover, the medical system 100 according to the present disclosure sets the control points 13 to be the plural points on the annotation 10 and can thereby more properly execute the production and the correction of the annotation 10 by using the control points 13.

The medical system 100 according to the present disclosure realizes the inputting relating to the annotation 10 and the inputting relating to the display of the first image data or the second image data each using a method different from that of each other. More specifically, in the medical system 100 according to the present disclosure, the inputting relating to the annotation 10 is performed by one hand of the user and the inputting relating to the display of the first image data or the second image data is performed by the other hand thereof. This input method resembles the input method conventionally performed by doctors when the doctors apply annotations, and the medical system 100 according to the present disclosure can therefore more intuitively and more efficiently realize the work by the user such as a doctor. Moreover, the medical system 100 according to the present disclosure can have the configuration for the user to more easily perform the inputting especially for annotations by free-hand (such as, for example, a pen-tablet capable of inputting using the pen 131a).

The medical system 100 according to the present disclosure can apply the high quality annotation 10 by the above, and the use of the medical system 100 may therefore produce new guidelines that explain the effects that have not been clarified so far, of the diagnosis and the drugs that use the pathological image data. Moreover, improvement of the precision of application of the annotation 10 by the machine learning is expected with the fact that learning is conducted using the learning data having the accurate annotation 10 is applied thereto. Furthermore, because the application of the annotation 10 can be performed in a shorter time period, for example, the time period can be reduced that is taken for the work for the pathologist to apply the annotation 10. It can therefore be stated that the medical system 100 according to the present disclosure is especially useful in the recent situation where pathologists are insufficient.

A preferred embodiment of the present disclosure has been described above in detail with reference to the accompanying drawings while the technical scope of the present disclosure is not limited to the above example. It is obvious to those skilled in the art of the present disclosure to be able to conceive various modification examples and various correction examples thereof within the scope of the technical idea descried in the appended claims, and it should be understood that the modification examples and the correction examples also naturally pertain to the technical scope of the present disclosure.

Moreover, the effects described herein are absolutely descriptive or exemplary, and are not limiting. In short, the technique according to the present disclosure can achieve other effects that are obvious to those skilled in the art from the description herein, together with the above effects or instead of the above effects.

In addition, the following configurations also pertain to the technical range of the present disclosure.

(1)

A medical system including:
  for pathological image data that is produced by imaging one observation target object and that includes pieces of image data having a plurality of different resolutions,
  a display control part that causes a displaying part to display thereon first image data having a first resolution of the plurality of different resolutions and second image data having a second resolution equal to the first resolution, or equal to or higher than the first resolution; and
  an annotation processing part that attaches an annotation to each of the first image data and the second image data on the basis of inputting by a user.

(2)

The medical system described in the above (1), in which the display control part superimposes the second image data on the first image data, to be displayed.

(3)

The medical system described in the above (2), in which the display control part superimposes a position in the first image data for which the inputting is performed by the user and a position in the second image data for which the inputting is performed by the user on each other, to be displayed.

(4)

The medical system described in any one of the above (1) to (3), in which
  the position in the first image data for which the inputting is performed by the user is in accordance with the position in the second image data for which the inputting is performed by the user.

(5)
The medical system described in any one of the above (1) to (4), in which
the first image data and the second image data include pieces of image data that each focus a position different from that of each other on the one observation target object.

(6)
The medical system described in any one of the above (1) to (5), in which
the first image data and the second image data include pieces of image data having targets that are dyed by a dyeing reagent and that are different from each other.

(7)
The medical system described in any one of the above (1) to (6), in which
at least either one of the first image data or the second image data includes image data that displays a result of an analysis.

(8)
The medical system described in any one of the above (1) to (7), in which
the second image data includes two or more pieces of image data whose display contents are different from each other.

(9)
The medical system described in any one of the above (1) to (8), in which
the annotation processing part attaches an annotation attached either one of the first image data or the second image data on the basis of the inputting by the user, to an other using SAL (Stain Alignment).

(10)
The medical system described in any one of the above (1) to (9), in which
the inputting by the user includes inputting by free-hand, and
the annotation processing part attaches the annotation drawn by the inputting by free-hand.

(11)
The medical system described in the above (10), in which
the annotation is attached to indicate a closed region included in each of the first image data and the second image data.

(12)
The medical system described in the above (11), in which
the annotation processing part sets control points that are a plurality of points on the annotation, and interpolates the control points using a predetermined method.

(13)
The medical system described in the above (12), in which
intervals among the control points are each determined in accordance with the second resolution.

(14)
The medical system described in the above (12) or (13), in which
the annotation processing part executes correction of the annotation using the control points on the basis of the inputting by the user.

(15)
The medical system described in the above (14), in which
the annotation processing part executes the correction for a first annotation attached first, using the control points included in the second annotation attached later.

(16)
The medical system described in the above (15), in which
the annotation processing part determines a correction range of the first annotation on the basis of a relative positional relation between first control points included in the first annotation and second control points included in the second annotation.

(17)
The medical system described in the above (16), in which
the second annotation includes a free line that is not closed, and
the annotation processing part executes the correction by connecting the second control points included in the second annotation on its both ends to any one of the first control points.

(18)
The medical system described in the above (17), in which
the annotation processing part executes the correction by connecting the second control points included in the second annotation on its both ends to the first control point for which an offset distance to each of the second control points is shortest.

(19)
The medical system described in the above (18), in which
the annotation processing part changes the first control point to be a connection target on the basis of an angle having a vertex that is either one of the first control point and the second control point connected to each other.

(20)
The medical system described in any one of the above (1) to (19), further including:
a first input part that receives inputting relating to the annotation; and
a second input part that receives inputting relating to the display of the first image data or the second image data, the second input part being different from the first input part.

(21)
The medical system described in the above (20), in which
either one of the first input part or the second input part receives inputting by a right hand of the user, and
an other thereof receives inputting by a left hand of the user.

(22)
A medical apparatus including:
for pathological image data that is produced by imaging one observation target object and that includes pieces of image data having a plurality of different resolutions,
a display control part that causes a displaying part to display thereon first image data having a first resolution of the plurality of different resolutions and second image data having a second resolution equal to the first resolution, or equal to or higher than the first resolution; and
an annotation processing part that attaches an annotation to each of the first image data and the second image data on the basis of inputting by a user.

(23)
The medical apparatus described in the above (22), further including:
the displaying part that displays thereon the first image data and the second image data on the basis of the control by the display control part.

(24)
A medical method executed by a computer, the medical method including the steps of:
for pathological image data that is produced by imaging one observation target object and that includes pieces of image data having a plurality of different resolutions,
causing a displaying part to display thereon first image data having a first resolution of the plurality of different resolutions and second image data having a second resolution equal to the first resolution, or equal to or higher than the first resolution; and
attaching an annotation to each of the first image data and the second image data on the basis of inputting by a user.

(25)
A medical system including:
an imaging apparatus producing pathological image data including pieces of image data having a plurality of different resolutions by imaging one observation target object; and
software used in processing for the pathological image data, in which
the software is executed by an information processing apparatus, and thereby realizes
causing a displaying part to display thereon first image data having a first resolution of the plurality of different resolutions and second image data having a second resolution equal to the first resolution, or equal to or higher than the first resolution, and
attaching an annotation to each of the first image data and the second image data on the basis of inputting by a user.

(26)
A medical system including:
a control part configured to receive pathological image data that is produced by imaging one observation target object and that includes first and second image data, the second image data relating to the observation target object but being different to the first image data,
a display control part that causes a displaying part to display thereon the first image data and the second image data; and
an annotation processing part that applies an annotation to each of the first image data and the second image data on a basis of input by a user.

(27)
The medical system according to (26), wherein
the display control part superimposes the second image data on the first image data, to be displayed.

(28)
The medical system according to (27), wherein
the display control part superimposes a position in the first image data for which the input is performed by the user and a position in the second image data for which the input is performed by the user on each other, to be displayed.

(29)
The medical system according to any of (26) to (28), wherein the second image data includes more detailed information than the first image data.

(30)
The medical system according to (29), wherein the more detailed information is a higher resolution image compared to the first image data.

(31)
The medical system according to any of (26) to (30), wherein
the position in the first image data for which the input is performed by the user is in accordance with the position in the second image data for which the input is performed by the user.

(32)
The medical system according to any of (26) to (31), wherein
the first image data and the second image data include pieces of image data having visual characteristics different from each other.

(33)
The medical system according to (32), wherein
the first image data and the second image data include pieces of image data that each focus a position different from that of each other on the one observation target object.

(34)
The medical system according to (32), wherein
the first image data and the second image data include pieces of image data having targets that are dyed by a dyeing reagent and that are different from each other.

(35)
The medical system according to any of (26) to (34), wherein
at least either one of the first image data or the second image data includes image data that displays a result of an analysis.

(36)
The medical system according to any of (26) to (35), wherein
the second image data includes two or more pieces of image data whose display contents are different from each other.

(37)
The medical system according to any of (26) to (36), wherein
the annotation processing part applies an annotation to either one of the first image data or the second image data on a basis of the input by the user, to an other using SAL (Stain Alignment).

(38)
The medical system according to any of (26) to (37), wherein
the input by the user includes input by free-hand, and
the annotation processing part applies the annotation drawn free-hand.

(39)
The medical system according to (38), wherein
the annotation is applied to indicate a closed region included in each of the first image data and the second image data.

(40)
The medical system according to (39), wherein
the annotation processing part sets control points that are a plurality of points on the annotation, and interpolates the control points using a predetermined method.

(41)
The medical system according to (40), wherein the difference between the first image and the second image is the resolution of the first image data and the second image data; and
intervals among the control points are each determined in accordance with the resolution of the second image data.

(42)
 The medical system according to (40), wherein
 the annotation processing part executes correction of the annotation using the control points on a basis of the input by the user.
(43)
 The medical system according to (42), wherein
 the annotation processing part executes the correction for a first annotation applied first, using the control points included in the second annotation applied later.
(44)
 The medical system according to (43), wherein
 the annotation processing part determines a correction range of the first annotation on a basis of a relative positional relation between first control points included in the first annotation and second control points included in the second annotation.
(45)
 The medical system according to (44), wherein
 the second annotation includes a free line that is not closed, and
 the annotation processing part executes the correction by connecting the second control points included in the second annotation on its both ends to any one of the first control points.
(46)
 The medical system according to (45), wherein
 the annotation processing part executes the correction by connecting the second control points included in the second annotation on its both ends to the first control point for which an offset distance to each of the second control points is shortest.
(47)
 The medical system according to (46), wherein
 the annotation processing part changes the first control point to be a connection target on a basis of an angle having a vertex that is either one of the first control point and the second control point that are connected to each other.
(48)
 The medical system according to any of (26) to (47), further including:
 a first input part that receives input relating to the annotation; and
 a second input part that receives input relating to the display of the first image data or the second image data, the second input part being different from the first input part.
(49)
 The medical system according to (48), wherein
 either one of the first input part or the second input part receives input by a right hand of the user, and
 an other thereof receives input by a left hand of the user.
(50)
 The medical system according to (26), wherein the annotation is associated with a co-ordinate in the image.
(51)
 A medical apparatus including:
 a control part configured to receive pathological image data that is produced by imaging one observation target object and that includes first and second image data, the second image data relating to the observation target object but being different to the first image data,
 a display control part that causes a displaying part to display thereon the first image data and the second image data; and
 an annotation processing part that applies an annotation to each of the first image data and the second image data on a basis of input by a user.
(52)
 The medical apparatus according to (51), further including:
 the displaying part that displays thereon the first image data and the second image data on a basis of the control by the display control part.
(53)
 The medical apparatus according to any of (51) to (52), further including:
 an image obtaining part configured to obtain the pathological image data.
(54)
 A medical method executed by a computer, the medical method including the steps of:
 receiving pathological image data that is produced by imaging one observation target object and that includes first and second image data, the second image data relating to the observation target object but being different to the first image data,
 causing a displaying part to display thereon the first image data and the second image data; and
 applying an annotation to each of the first image data and the second image data on a basis of input by a user.
(55)
 A medical system including:
 an imaging apparatus producing pathological image data including first and second image data, the second image data relating to the observation target object but being different to the first image data; and
 software used in processing for the pathological image data, wherein
 the software is executed by an information processing apparatus, and thereby realizes
 causing a displaying part to display thereon the first image data and the second image data, and
 applying an annotation to each of the first image data and the second image data on a basis of input by a user.

REFERENCE SIGNS LIST

100 Medical system
110 Image obtaining part
120 Control part
121 Display control part
122 Annotation processing part
123 Image analyzing part
130 Input part
131 First input part
132 Second input part
140 Displaying part
150 Storing part

The invention claimed is:
1. A medical system comprising: processing circuitry configured to: receive pathological image data that is produced by imaging one observation target object and that includes first and second image data, the second image data relating to the observation target object but being different from the first image data; cause a display to display thereon the first image data and the second image data; and apply an annotation to each of the first image data and the second image data on a basis of input by a user, wherein the processing circuitry is further configured to set control points that include a plurality of points on the annotation, and to interpolate the control points using a predetermined method, and wherein a difference between the first image data and the second image data is a resolution of the first image data and the second image data, and intervals among the control points are each determined in accordance with the resolution of the second image data.

2. The medical system according to claim 1, wherein the processing circuitry is configured to superimpose the second image data on the first image data, to be displayed.

3. The medical system according to claim 2, wherein the processing circuitry is configured to superimpose a position in the first image data for which the input is performed by the user and a position in the second image data for which the input is performed by the user on each other, to be displayed.

4. The medical system according to claim 1, wherein the second image data includes more detailed visual information than the first image data.

5. The medical system according to claim 1, wherein a position in the first image data for which the input is performed by the user is in accordance with a position in the second image data for which the input is performed by the user.

6. The medical system according to claim 1, wherein the first image data and the second image data include pieces of image data having visual characteristics different from each other.

7. The medical system according to claim 6, wherein the first image data and the second image data include pieces of image data that each focus a position different from that of each other on the one observation target object.

8. The medical system according to claim 6, wherein the first image data and the second image data include pieces of image data having targets that are dyed by a dyeing reagent and that are different from each other.

9. The medical system according to claim 1, wherein at least either one of the first image data or the second image data includes image data that displays a result of an analysis.

10. The medical system according to claim 1, wherein the second image data includes two or more pieces of image data whose display contents are different from each other.

11. The medical system according to claim 1, wherein the processing circuitry is configured to apply an annotation to either one of the first image data or the second image data on a basis of the input by the user, using SAL (Stain Alignment).

12. The medical system according to claim 1, wherein the input by the user includes input by free-hand, and the processing circuitry is configured to apply the annotation drawn free-hand.

13. The medical system according to claim 12, wherein the annotation is applied to indicate a closed region included in each of the first image data and the second image data.

14. The medical system according to claim 1, further comprising: a first input device that receives input relating to the annotation; and a second input device that receives input relating to the display of the first image data or the second image data, the second input device being different from the first input device.

15. The medical system according to claim 14, wherein either one of the first input device or the second input device receives input by a right hand of the user, and another thereof receives input by a left hand of the user.

16. The medical system according to claim 1, wherein the annotation is associated with a co-ordinate in the image.

17. A medical system comprising: processing circuitry configured to: receive pathological image data that is produced by imaging one observation target object and that includes first and second image data, the second image data relating to the observation target object but being different from the first image data; cause a display to display thereon the first image data and the second image data; and apply an annotation to each of the first image data and the second image data on a basis of input by a user, wherein the processing circuitry is configured to set control points that include a plurality of points on the annotation, and to interpolate the control points using a predetermined method, and wherein the processing circuitry is further configured to execute correction of the annotation using the control points on a basis of the input by the user.

18. The medical system according to claim 17, wherein the processing circuitry is configured to execute the correction for a first annotation applied first, using the control points included in the second annotation applied later.

19. The medical system according to claim 18, wherein the processing circuitry is configured to determine a correction range of the first annotation on a basis of a relative positional relation between first control points included in the first annotation and second control points included in the second annotation.

20. The medical system according to claim 19, wherein the second annotation includes a free line that is not closed, and the processing circuitry is configured to execute the correction by connecting the second control points included in the second annotation on its both ends to any one of the first control points.

21. The medical system according to claim 20, wherein the processing circuitry is configured to execute the correction by connecting the second control points included in the second annotation on its both ends to the first control point for which an offset distance to each of the second control points is shortest.

22. The medical system according to claim 21, wherein the processing circuitry is configured to change the first control point to be a connection target on a basis of an angle having a vertex that is either one of the first control point and the second control point that are connected to each other.

23. A medical apparatus comprising: processing circuitry configured to: receive pathological image data that is produced by imaging one observation target object and that includes first and second image data, the second image data relating to the observation target object but being different from the first image data; cause a display to display thereon the first image data and the second image data; and apply an annotation to each of the first image data and the second image data on a basis of input by a user, wherein the processing circuitry is further configured to set control points that include a plurality of points on the annotation, and to interpolate the control points using a predetermined method, and wherein a difference between the first image data and the second image data is a resolution of the first image data and the second image data, and intervals among the control points are each determined in accordance with the resolution of the second image data.

24. The medical apparatus according to claim 23, further comprising: the display that displays thereon the first image data and the second image data.

25. The medical apparatus according to claim 23, further comprising: an image capture device configured to obtain the pathological image data.

26. A medical method executed by a computer, the medical method comprising: receiving pathological image data that is produced by imaging one observation target object and that includes first and second image data, the second image data relating to the observation target object but being different from the first image data; causing a display to display thereon the first image data and the second image data; applying an annotation to each of the first image data and the second image data on a basis of input by a user; setting control points that include a plurality of points on the annotation; and interpolating the control points using a predetermined method, wherein a difference between the first image data and the second image data is a resolution of the first image data and the second image data; and intervals among the control points are each determined in accordance with the resolution of the second image data.

27. A medical system comprising: an imaging apparatus producing pathological image data including first and second image data, the second image data relating to the observation target object but being different from the first image data; and processing circuitry configured to: cause a display to display thereon the first image data and the second image data, and apply an annotation to each of the first image data and the second image data on a basis of input by a user, wherein the processing circuitry is further configured to set control points that include a plurality of points on the annotation, and to interpolate the control points using a predetermined method, and wherein a difference between the first image data and the second image data is a resolution of the first image data and the second image data, and intervals among the control points are each determined in accordance with the resolution of the second image data.

* * * * *